(12) United States Patent
Wing et al.

(10) Patent No.: US 10,734,825 B2
(45) Date of Patent: Aug. 4, 2020

(54) APPARATUS FOR TREATING A RESPIRATORY DISORDER WITH A POWER SOURCE CONNECTION

(71) Applicant: RESMED PARIS SAS, Moissy, Cramayel (FR)

(72) Inventors: Alex Crawford Wing, Sydney (AU); Christopher Kingsley Blunsden, Sydney (AU); Korn Sar, Sydney (AU); David Creusot, Sydney (AU)

(73) Assignee: ResMed Paris SAS, Moissy-Cramayel (FR)

( * ) Notice: Subject to any disclaimer, the term of this patent is extended or adjusted under 35 U.S.C. 154(b) by 0 days.

(21) Appl. No.: 16/445,847

(22) Filed: Jun. 19, 2019

(65) Prior Publication Data

US 2019/0372369 A1    Dec. 5, 2019

Related U.S. Application Data

(63) Continuation of application No. 14/528,573, filed on Oct. 30, 2014, now Pat. No. 10,381,849.

(30) Foreign Application Priority Data

Oct. 31, 2013    (EP) .................................... 13306491

(51) Int. Cl.
  *G05D 11/00*    (2006.01)
  *H02J 7/00*    (2006.01)
  (Continued)

(52) U.S. Cl.
  CPC ......... *H02J 7/0045* (2013.01); *A61M 16/026* (2017.08); *G05D 16/20* (2013.01);
  (Continued)

(58) Field of Classification Search
  CPC .. A61M 16/125; A61M 16/109; A61M 11/00; A61M 15/00; A61M 16/0066;
  (Continued)

(56) References Cited

U.S. PATENT DOCUMENTS 4,944,310 A    7/1990    Sullivan
5,563,493 A    10/1996    Matsuda et al.
(Continued)

FOREIGN PATENT DOCUMENTS

CN    1135113 A    11/1996
CN    1832295 A    9/2006
(Continued)

OTHER PUBLICATIONS

EP Search Report dated Jul. 25, 2019 in corresponding EP Application 19169325.8.
(Continued)

*Primary Examiner* — Tuan A Vu
(74) *Attorney, Agent, or Firm* — Nixon & Vanderhye P.C.

(57) ABSTRACT

A respiratory device, such as a ventilator, for use in treating respiratory disorders and for preventing respiratory disorders. The respiratory device is configured to be powered from a range of different power sources including an internal battery, an external battery, AC power source or a DC power source. The device may be electrically connectable to a plurality of external batteries in a series and the power from each external battery is used sequentially along the series. A controller of the respiratory device is configured to detect the connection of the different power sources and control use of the different power sources using a power priority scheme. The controller may determine an estimate of the total available battery capacity from all the electrically connected batteries and display the total battery capacity on a user interface display of the device.

16 Claims, 18 Drawing Sheets

(51) Int. Cl.
*G05D 16/20* (2006.01)
*A61M 16/00* (2006.01)
*H01M 10/48* (2006.01)
*A61M 16/20* (2006.01)

(52) U.S. Cl.
CPC .......... *H02J 7/0013* (2013.01); *H02J 7/0036* (2013.01); *H02J 7/0063* (2013.01); *A61M 16/205* (2014.02); *A61M 2016/0039* (2013.01); *A61M 2202/0208* (2013.01); *A61M 2205/8206* (2013.01); *A61M 2205/8237* (2013.01); *A61M 2205/8262* (2013.01); *H01M 10/482* (2013.01); *H02J 7/0048* (2020.01); *H02J 2007/0067* (2013.01)

(58) Field of Classification Search
CPC ...... A61M 16/0036; A61M 2205/8206; A61M 2205/8262; G04C 10/00; H01M 10/441; H02J 1/00; H02J 7/0013; H02J 7/0045
See application file for complete search history.

(56) References Cited

U.S. PATENT DOCUMENTS

| | | | |
|---|---|---|---|
| 5,652,499 | A | 7/1997 | Morita et al. |
| 5,710,501 | A | 1/1998 | Van Phuoc |
| 6,329,794 | B1 | 12/2001 | Oeda et al. |
| 6,421,261 | B1* | 7/2002 | Fujisawa ............... G04C 10/00 363/127 |
| 6,532,959 | B1 | 3/2003 | Berthon-Jones |
| 7,975,687 | B2 | 7/2011 | Gründler et al. |
| 2004/0155628 | A1* | 8/2004 | Liscio ................. A61B 5/0046 320/127 |
| 2006/0139005 | A1 | 6/2006 | Niculae et al. |
| 2008/0180059 | A1 | 7/2008 | Carrier |
| 2009/0058665 | A1 | 3/2009 | Lamb |
| 2009/0084381 | A1* | 4/2009 | DeVries .............. A61M 16/125 128/204.21 |
| 2010/0065054 | A1 | 3/2010 | Bowman et al. |
| 2010/0292544 | A1 | 11/2010 | Sherman |
| 2011/0162647 | A1* | 7/2011 | Huby .................. A61M 16/109 128/203.14 |
| 2011/0169455 | A1 | 7/2011 | Nagase |
| 2011/0197882 | A1* | 8/2011 | Truschel ............. A61M 16/125 128/204.18 |
| 2011/0234162 | A1* | 9/2011 | Kinoshita ........... H01M 10/441 320/116 |
| 2011/0309676 | A1* | 12/2011 | Terrell ...................... H02J 1/00 307/23 |
| 2012/0130153 | A1 | 5/2012 | Bolyard |
| 2012/0256568 | A1 | 10/2012 | Lee |
| 2012/0313437 | A1 | 12/2012 | Latham |
| 2013/0263854 | A1 | 10/2013 | Taylor et al. |

FOREIGN PATENT DOCUMENTS

| | | |
|---|---|---|
| CN | 102035235 | 4/2011 |
| CN | 102165626 | 8/2011 |
| CN | 102187545 | 9/2011 |
| CN | 202166892 U | 3/2012 |
| CN | 202183612 U | 4/2012 |
| CN | 102593893 | 7/2012 |
| CN | 102931694 | 2/2013 |
| DE | 20 2011 106 203 | 1/2012 |
| EP | 0 607 041 A2 | 7/1994 |
| GB | 2359605 | 8/2001 |
| JP | 6-217464 | 8/1994 |
| JP | 2008-136664 | 6/2008 |
| WO | 2002/09255 A1 | 1/2002 |
| WO | 2010/044037 | 4/2010 |
| WO | WO 2011/054038 A1 | 5/2011 |

OTHER PUBLICATIONS

English translation of CN Third Office Action dated Aug. 1, 2019 in corresponding CN Application 201480059531.6.
European Communication issued in Application No. 13 306 491.5-1202 dated Mar. 20, 2018, 6 pages.
European Search Report issued in Application No. 13306491.5-1804 dated Jul. 15, 2014, 16 pages.
Chinese Office Action with English translation issued in Application No. 201480059531.6 dated Apr. 28, 2018, 17 pages.
Japanese Office Action with English translation issued in Application No. 2014-222297 dated Oct. 2, 2018 10 pages.
Notification Concerning Transmittal of International Preliminary Report on Patentability, including Written Opinion of the International Searching Authority, dated May 12, 2016 in International Application No. PCT/EP2014/073351 (14 pages).
Second Chinese Office Action and English Translation for Chinese Application No. 201480059531.6, 12 pages, dated Jan. 21, 2019.
Taylor, U.S. Appl. No. 13/624,167, filed Sep. 21, 2012.

* cited by examiner

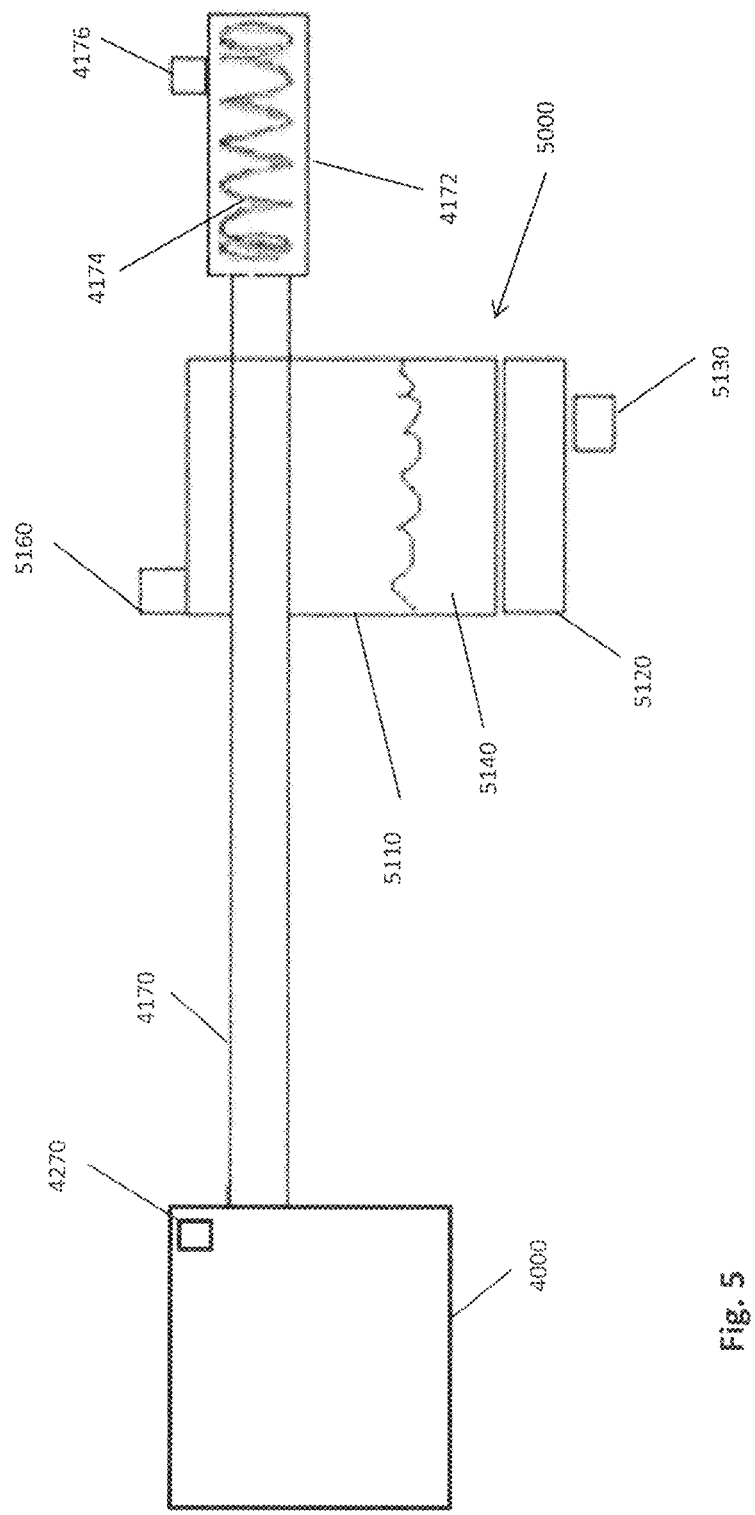

APPARATUS FOR TREATING A RESPIRATORY DISORDER WITH A POWER SOURCE CONNECTION

1 CROSS-REFERENCE TO RELATED APPLICATIONS

This application is a continuation application of U.S. application Ser. No. 14/528,573, filed Oct. 30, 2014, now allowed; which claims priority to European Patent Application No. 13 30 6491.5, filed 31 Oct. 2013, the entire contents of which are hereby incorporated herein by reference.

2 COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

3 BACKGROUND OF THE INVENTION

3.1 Field of the Invention

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

3.2 Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

3.2.1 Systems

One known product used for treating sleep disordered breathing is the S9 Sleep Therapy System, manufactured by ResMed. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

3.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body. The ventilator support is provided by a mask or nasal interface. NIV has been used to treat OHS, COPD, MD and Chest Wall disorders. Invasive ventilation (IV) provides ventilatory support to patient's that are no longer able to effectively breathe themselves and is provided using a tracheostomy tube or an endotracheal tube.

Ventilators also control the timing and pressure of breaths pumped into the patient and monitors the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

3.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping or throughout the day.

A tracheostomy tube or endotracheal tube are other forms of patient interfaces that may be used for invasive ventilation.

3.2.4 Devices

The air at positive pressure may be supplied to the airway of a patient by a Positive airway pressure (PAP) device such as a motor-driven blower. The outlet of the blower is connected via a flexible delivery conduit to a patient interface as described above.

Ventilators typically include a flow generator, an inlet filter, a patient interface, an air delivery conduit connecting the flow generator to the patient interface, various sensors and a microprocessor-based controller. The patient interface may include a mask, nasal prongs or a tracheostomy or endotracheal tube as described above. The flow generator may include a servo-controlled motor, volute and an impeller that forms a blower. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the flow generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The apparatus may optionally include a humidifier and/or heater elements in the path of the air delivery circuit. The controller may include data storage capacity with or without integrated data retrieval and display functions.

3.2.5 Humidifier

Respiratory apparatuses commonly have the ability to alter the humidity of the breathable gas in order to reduce drying of the patient's airway and consequent patient discomfort and associated complications. A humidifier may be located between the flow generator or PAP device or ventilator and the patient interface or before the flow generator or PAP device or Ventilator. The use of a humidifier produces humidified gas that minimizes drying of the nasal mucosa and increases patient airway comfort. In addition in cooler climates, warm air applied generally to the face area in and about the patient interface is more comfortable than cold air.

Humidity refers to the quantity of water vapour present in the air. It is commonly measured in two ways:
(1) Absolute Humidity (AH) is the actual content of water recorded in terms of weight per volume—usually in grams per cubic meter (g/m3) or milligrams per liter (mg/L).
(2) Relative Humidity (RH) is a percentage expression of the actual water vapour content of a gas compared to its capacity to carry water at any given temperature.

The capacity of air to hold water vapour increases as the temperature of the air increases. This means that for air with a stable AH, the RH will decline as the temperature of the air is increased. Conversely, for air saturated with water (100% RH), if the temperature is reduced then the excess water will condense out. Air breathed by humans is generally naturally heated and humidified by the airway to reach a temperature of 37° C. and 100% humidity. At this temperature the AH humidity is 44 mg/L.

Respiratory humidifiers are available in many forms and may be a standalone device that is coupled to a respiratory device via a air delivery tube, is integrated with the respiratory device or configured to be directly coupled to the relevant respiratory apparatus. While passive humidifiers can provide some relief, generally a heated humidifier is required to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator or device, and a gas outlet adapted to be connected to an air delivery conduit that delivers the humidified gas to the patient interface.

Heated passover humidification is one common form of humidification used with a PAP device. In such systems the heating element may be incorporated in a heater plate which sits under, and is in thermal contact with, the water tub. Thus, heat is transferred from the heater plate to the water reservoir primarily by conduction. The air flow from the PAP device or flow generator or ventilator passes over the heated water in the water tub resulting in water vapour being taken up by the air flow. The ResMed H4i™ and H5i™ Humidifiers are examples of such heated passover humidification systems that are used in combination with ResMed S8 and S9 CPAP systems respectively.

Other humidification systems may also be used such as a bubble or diffuser humidifier, a jet humidifier or a wicking humidifier.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

3.2.6 Air Circuits

Air circuits may include a single limb circuit or air delivery conduit as shown in FIG. 1. A single limb circuit may be used with an intentional leak vent. The vent may be provided as an independent part, such as an anti-asphyxia valve, fitted to an air delivery tube or the vent may be incorporated in as part of the patient interface. The air delivery tube is connected to the outlet of the device, e.g. ventilator or humidifier. In this single limb circuit arrangement the inspiratory air or gas is from the device through the air delivery conduit to the patient interface for delivery to the patient and the patient's exhaled gas is exhausted through the vent. The ventilator provides a positive pressure at the vent to ensure the patient exhalant is exhausted.

In an alternative arrangement a single limb circuit may be used with a proximal pneumatic valve. The proximal pneumatic valve is provided near the patient interface end of the air delivery conduit. The opposite end of the air delivery tube is connected to the outlet of the device, e.g. ventilator or humidifier. A small tube is also connected between the device and the proximal pneumatic valve to provide a pressure control line. The device applies a control pressure to the proximal pneumatic valve to control opening and closing of an exhaust port of the proximal pneumatic valve. During inhalation, the valve is fully closed, directing all air flow to the patient interface. During exhalation, the valve is proportionally controlled to permit the patient to exhale out of the exhaust port but at a specified back-pressure (known as the Positive End Expiratory Pressure (PEEP)). The ventilator also continues to output a bias-flow to ensure accurate control of PEEP, and to offset any unintentional leak at the patient interface. Air pressure at the patient may be monitored, using a pressure sense line that is connected to a proximal pressure sensor within the ventilator.

In a further arrangement a double limb circuit may be used. A double limb circuit comprises two tubes: an inspiratory tube that delivers air from the ventilator to the patient during inspiration; and an expiratory tube that delivers expired air from the patient to an expiratory port of the ventilator and then out an exhaust port. Geometrically the two tubes may be arranged side-by-side or co-axially. Air flow between the expiratory port and the exhaust port may be regulated by a pneumatic valve located internally within the ventilator.

During inspiration, the valve is fully closed, directing all air flow to the patient. During expiration, the valve is proportionally controlled to permit the patient to exhale out of the exhaust port but at a specified PEEP pressure. The ventilator also continues to output a bias-flow to ensure accurate control of PEEP, and to offset any unintentional leak at the patient interface. Air pressure at the patient may be monitored during inspiration via a proximal pressure sensor within the ventilator connected to the expiratory tube; and during expiration via an output pressure sensor connected to the inspiratory tube.

Heated single limb or double limb air delivery circuits may also be used to prevent rainout from occurring within the air delivery circuits.

4 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

One form of the present technology comprises an apparatus for treating a respiratory disorder electrically connected to a plurality of external batteries connected in series.

Another aspect of one form of the present technology is a ventilator capable of being electrically connected to a plurality external batteries electrically connected in series.

Another aspect of one form of the present technology is a method of determining an estimate of available battery capacity from two or more battery power sources electrically connected to a respiratory device. Battery capacity may include for example battery remaining run time or battery remaining charge.

Another aspect of one form of the present technology includes an apparatus for treating a respiratory disorder comprising a housing, a user interface display, a pressure source to provide a supply of pressurized gas, a controller configured to control the pressure source, a power source connection configured to receive an electrical connection of a power source to provide power for the apparatus, and a plurality of external batteries electrically connected in a series to the power source connection.

The controller of the apparatus may be configured to detect the connection of the plurality of external batteries and control the supply of power to the apparatus. Furthermore, in use the external battery of the plurality of external batteries being used to provide the supply of power for the apparatus may be the power supplying external battery and each of the plurality of external batteries may be used as the power source sequentially with the external battery closest to the power source connection being the first external battery to be used as the power source. Each external battery of the plurality of external batteries may be connected to an adjacent external battery using an electrical cable. The external battery closest to the ventilator may be the last external battery to be used. The recharging of the series of external batteries may be performed in the reverse order, such that the external battery closest to the ventilator is recharged first.

In an alternative arrangement the external batteries may be used in series as a power source with the external battery closest to the ventilator being the first external battery to be used. The recharging of the external batteries may also be performed in series with the external battery closest to the ventilator being recharged last.

In some aspect the apparatus may also comprise an internal battery configured to be received within the housing and in use the internal battery is used as the power source after all the power from the external batteries is depleted.

In some aspect the apparatus may also comprise an alternating current (AC) power supply connectable in the series to the plurality of external batteries, and in use when the AC power supply is connected the AC power supply is used as the power source.

In some aspect the apparatus may also comprise a direct current (DC) power supply connectable in the series to the plurality of external batteries, and in use when the DC power supply is connected the DC power supply is used as the power source.

In some aspects upon receiving a power capacity request from the controller each of the plurality of external batteries is capable of determining an estimate of its own remaining capacity. The external batteries remaining capacity may be used to determine an estimate of the total external batteries remaining run time or state of charge. The total external batteries remaining run time may be determined as a function remaining run time of the power supplying external battery.

In some aspects the plurality of external batteries includes a downstream external battery and an upstream external battery, wherein the upstream external battery is electrically connected to the power source connection and the downstream external battery is electrically connected in the series to the upstream external battery. The upstream external battery may be connected to the power source connection using an electrical cable. Furthermore, one or more further external batteries may be electrically connected between the downstream external battery and the upstream external battery.

In some aspects the upstream external battery is configured to send the determined estimate of the upstream external batteries remaining capacity to the downstream external battery. Each of the one or more further external batteries may be configured to send the determined estimate of the external battery remaining capacity along the series to the downstream external battery. The downstream external battery may be configured to determine a total external battery remaining capacity or state of charge from all the external batteries electrically connected in the series. The downstream external battery may be configured to determine the total external battery remaining run time from all the external batteries electrically connected in the series as a function of a remaining run time of the upstream external battery being used to provide the power to run the apparatus.

In some aspects upon receiving a remaining capacity request from the controller the internal battery may be capable of determining an estimate of the internal battery remaining power capacity. The internal battery remaining capacity may be used to determine an estimate of internal battery remaining run time. The internal battery remaining run time may be determined as a function of a remaining run time of the internal battery when the internal battery is being used to provide the power to run the apparatus or the power supplying external battery when one of the plurality of external batteries is being used to run the apparatus.

In some aspects the controller may be configured to calculate an estimate of a total battery remaining capacity or total state of charge of the plurality of external batteries and the internal batteries. The controller may be configured to calculate an estimate of a total battery remaining run time of the plurality of external batteries and the internal batteries. In some aspects the user interface display may be configured to display the estimate of the total battery remaining capacity, the total battery remaining charge and/or the estimate of the total battery remaining run time.

In some aspects the apparatus may be a ventilator.

An aspect of the present technology includes a method of determining an estimate of a total available battery capacity from two or more battery power sources electrically connected to a respiratory device, the respiratory device comprising a controller configured to perform the method of request an estimate of available capacity from a first battery power source to provide a first battery capacity level, request an estimate of available capacity from a second battery power source to provide a second battery capacity level, and combine the first battery capacity level and the second battery capacity level to determine an estimate of the total available battery capacity.

In some aspects the total available battery capacity is an estimate of a total remaining capacity or a total remaining charge or a total state of charge from the first battery source and the second battery source.

In some aspects the first battery source is at least one external battery electrically connected to the respiratory device and the second battery source is an internal battery located within the respiratory device. The first battery source may include a plurality of external batteries connected in series, each of the plurality of external batteries including an input port and output port configured to receive an electrical cable therebetween. The plurality of external batteries may include a downstream external battery, the output port of the downstream external battery is electrically coupled to the respiratory device via an electrical cable and the input port of the downstream external battery is electrically coupled via an electrical cable to the output port of a second external battery of the plurality of external batteries. Furthermore, each of the plurality of external batteries may be electrically coupled to an adjacent external battery via an electrical cable connected between the input port of one of the plurality of external batteries and the output port of the adjacent external battery. The method may further include each external battery providing an estimate of available capacity and sending the available capacity via the electrical cables along the series to the upstream external battery. The method may also include displaying the total available battery capacity on a user interface display of the respiratory device.

Another aspect of one form of the present technology is a respiratory device having improved power efficiency.

Another aspect of one form of the present technology is a respiratory device to provide a supply of breathable gas to a patient breathing in successive cycles, each cycle including an inspiration phase and an expiration phase, the respiratory device comprising a blower including a motor configured to accelerate to reach an inspiration pressure provided during the inspiration phase and decelerate to reach an expiration pressure provided during the expiration phase; a first power source arranged to supply power to run the motor of the blower; and an energy storage unit configured to store energy generated by the motor when the motor decelerates; wherein when a voltage present in the energy storage unit exceeds a first threshold, the supply of power from the first power source to the motor is turned off and the motor is energized by the energy in the energy storage unit and when the voltage in the energy storage unit falls below a second threshold the supply of power from the first power source to the motor is turned on.

In some aspects the energy storage unit includes at least one capacitor or super capacitor. In some aspects the respiratory device further comprises a regulator switch that monitors the voltage of the energy storage unit and switches the supply of power to the motor from the first power source on and off.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

5 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

5.1 Treatment Systems

FIG. 1 shows a system in accordance with the present technology. A patient 1000 wearing a patient interface 3000, receives a supply of air at positive pressure from a device or ventilator 4000. Air from the device is humidified in a humidifier 5000, and passes along an air circuit 4170 to the patient 1000. In an alternative arrangement (not shown) the humidifier may be located upstream or before the device or ventilator 4000.

5.2 Therapy 5.2.1 Respiratory System

5.3 Patient Interface

Figure 1:
Figure 2A:
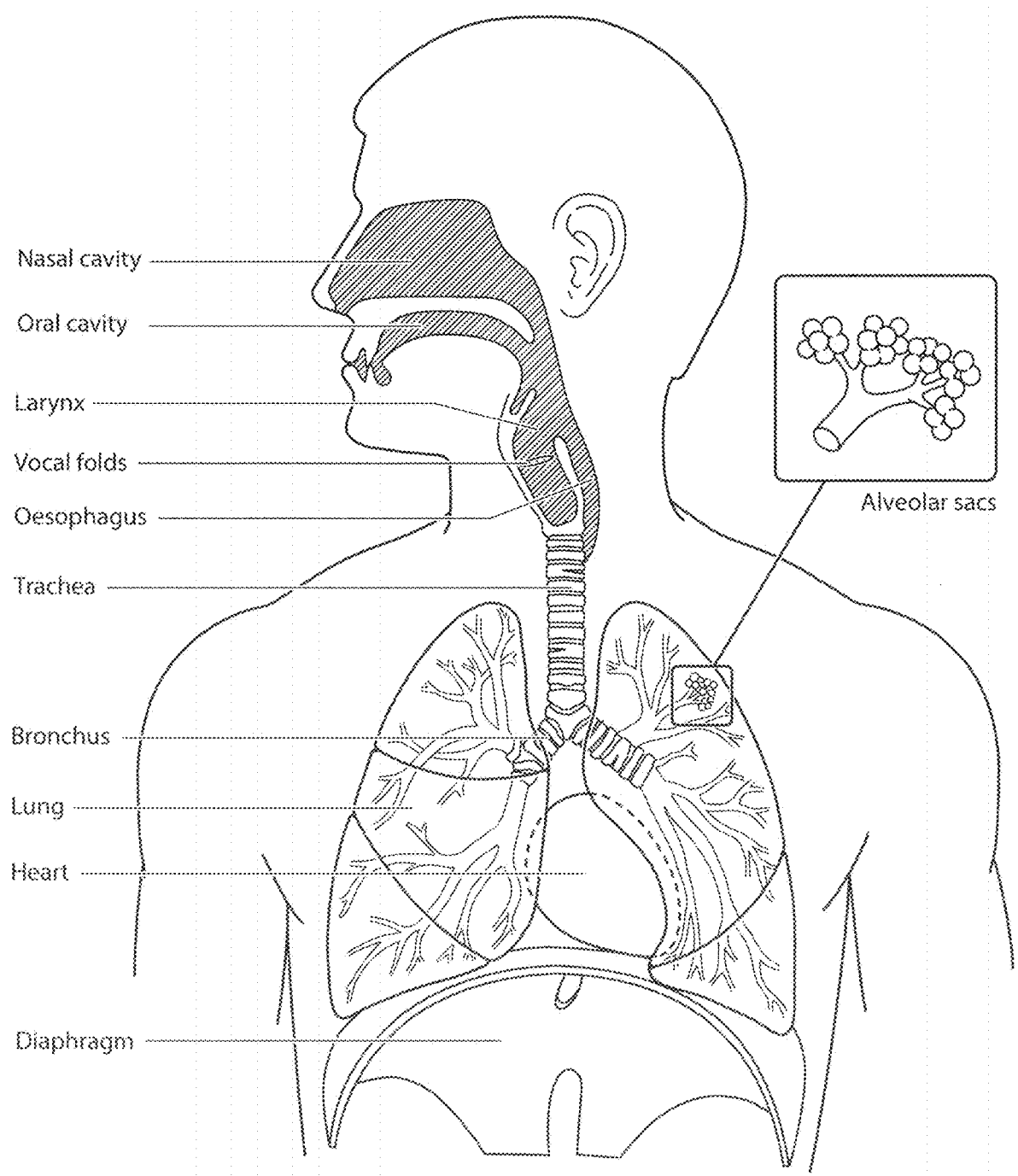
FIG. 2a shows an overview of a human respiratory system including the nasal and oral cavities, the larynx, vocal folds, oesophagus, trachea, bronchus, lung, alveolar sacs, heart and diaphragm.
Figure 2B:
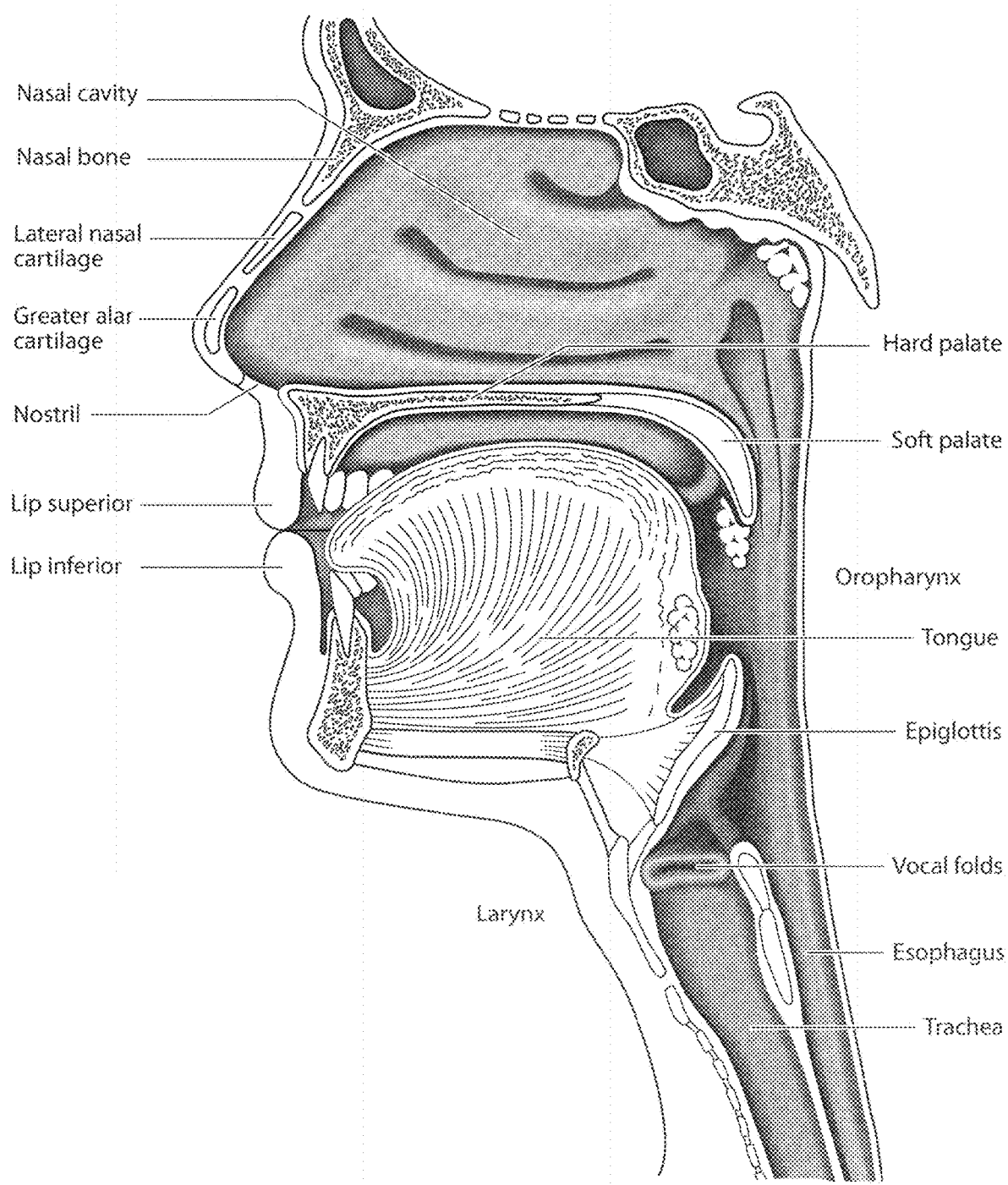
FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 3A:
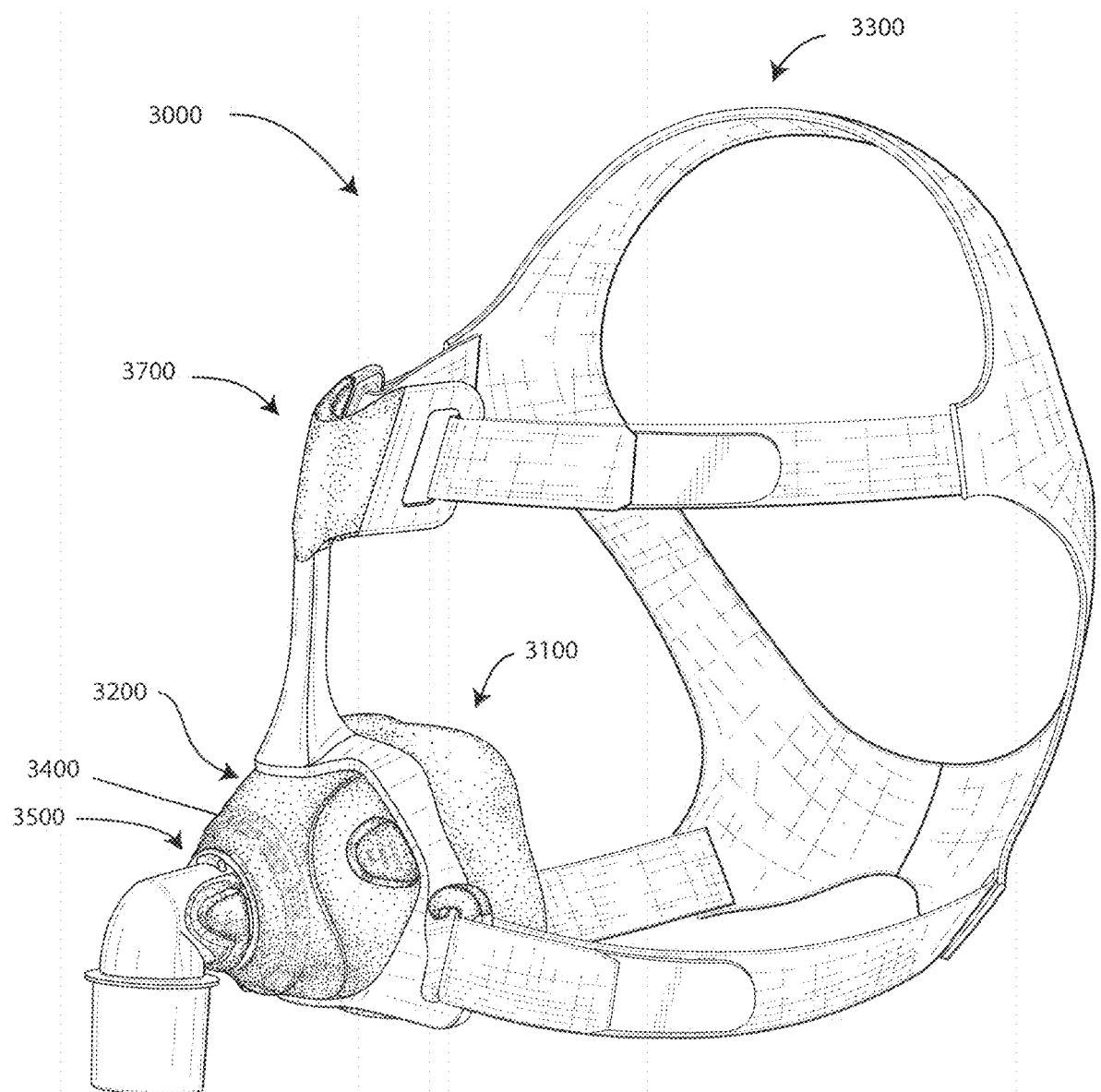

FIG. 3a shows an example patient interface in accordance with one form of the present technology.

5.4 Ventilator Device

Figure 4A:
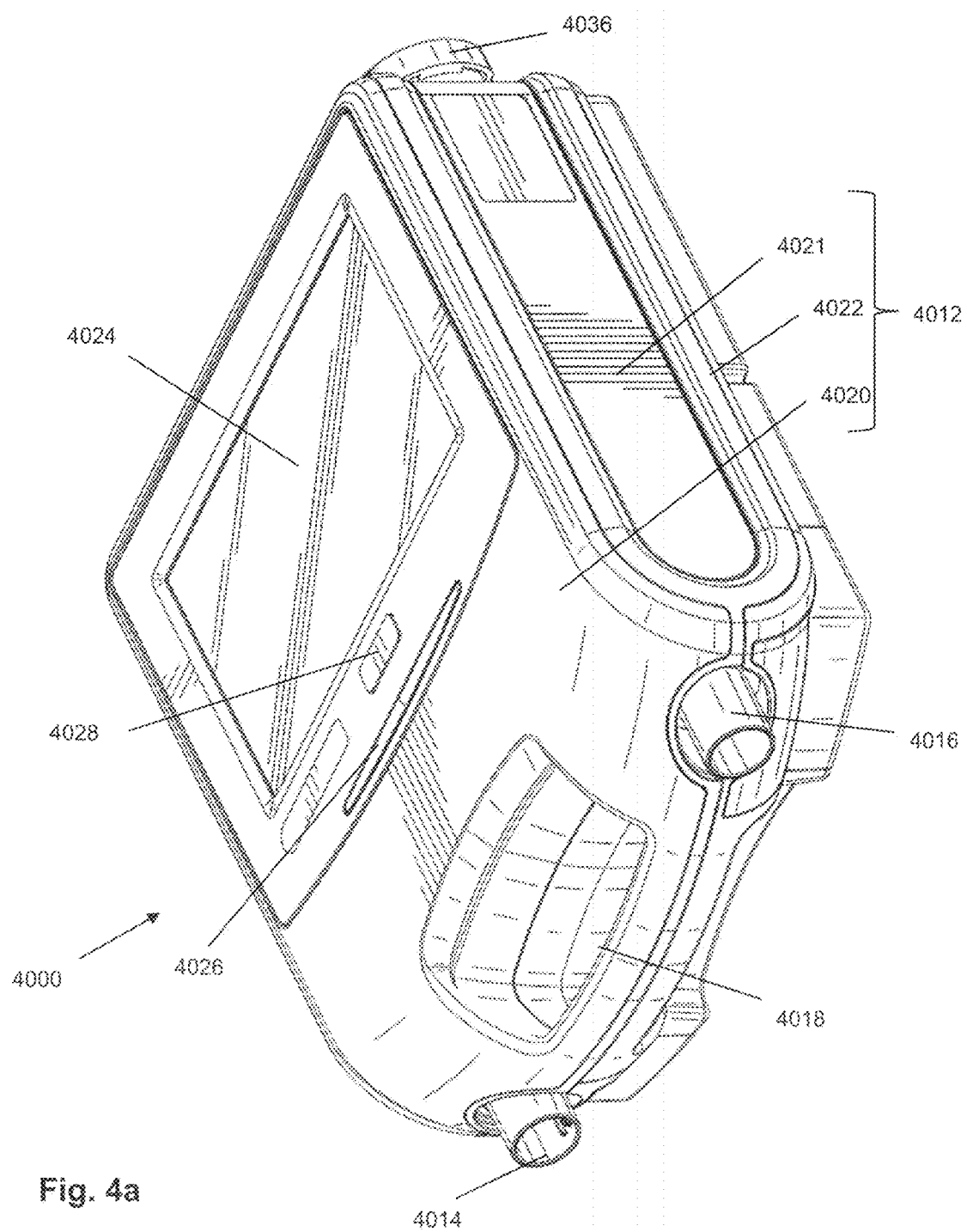

FIG. 4a shows a perspective view of a ventilator device in accordance with one form of the present technology.

Figure 4B:
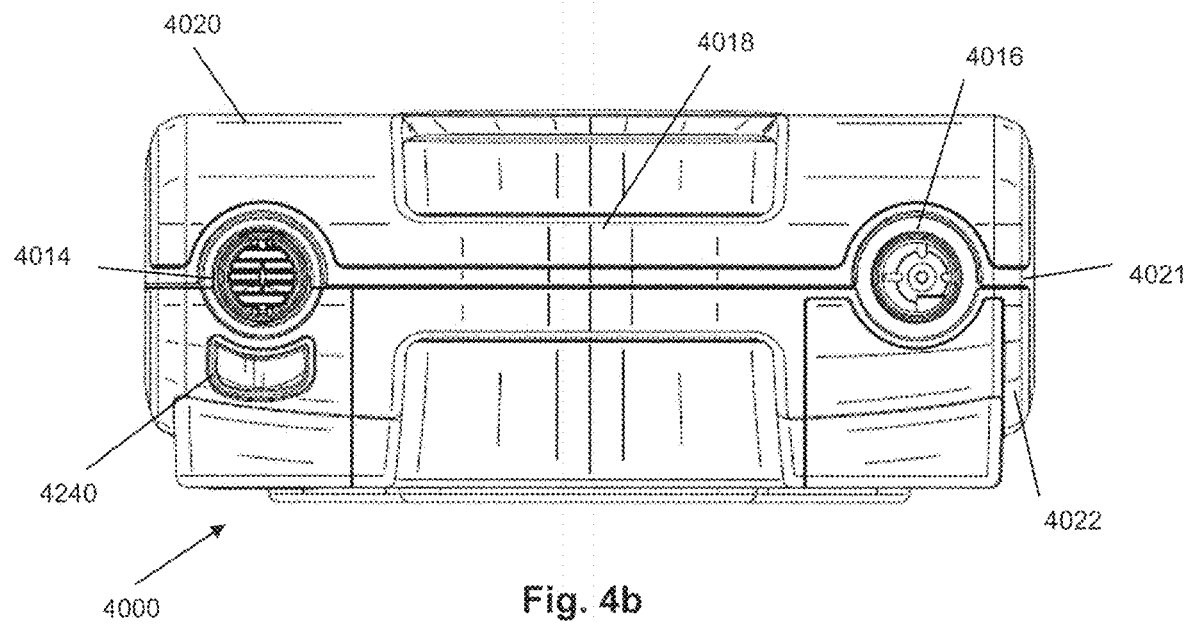

FIG. 4b shows a front view of the ventilator device of FIG. 4a

Figure 4C:
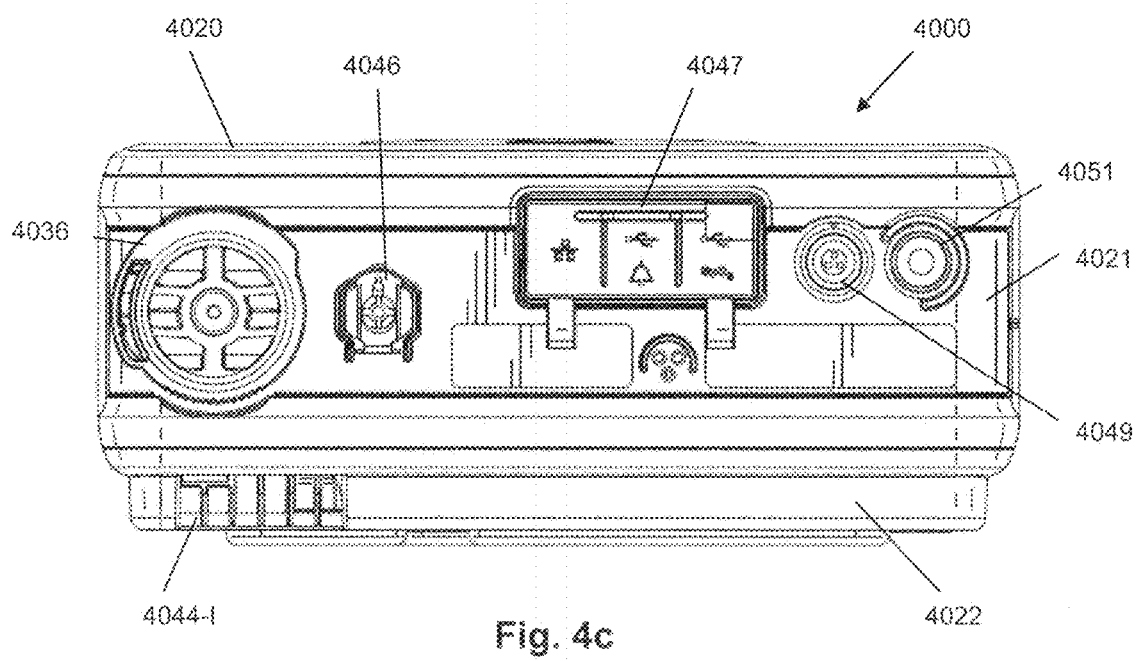

FIG. 4c shows a rear view of the ventilator device of FIG. 4a.

Figure 4D:
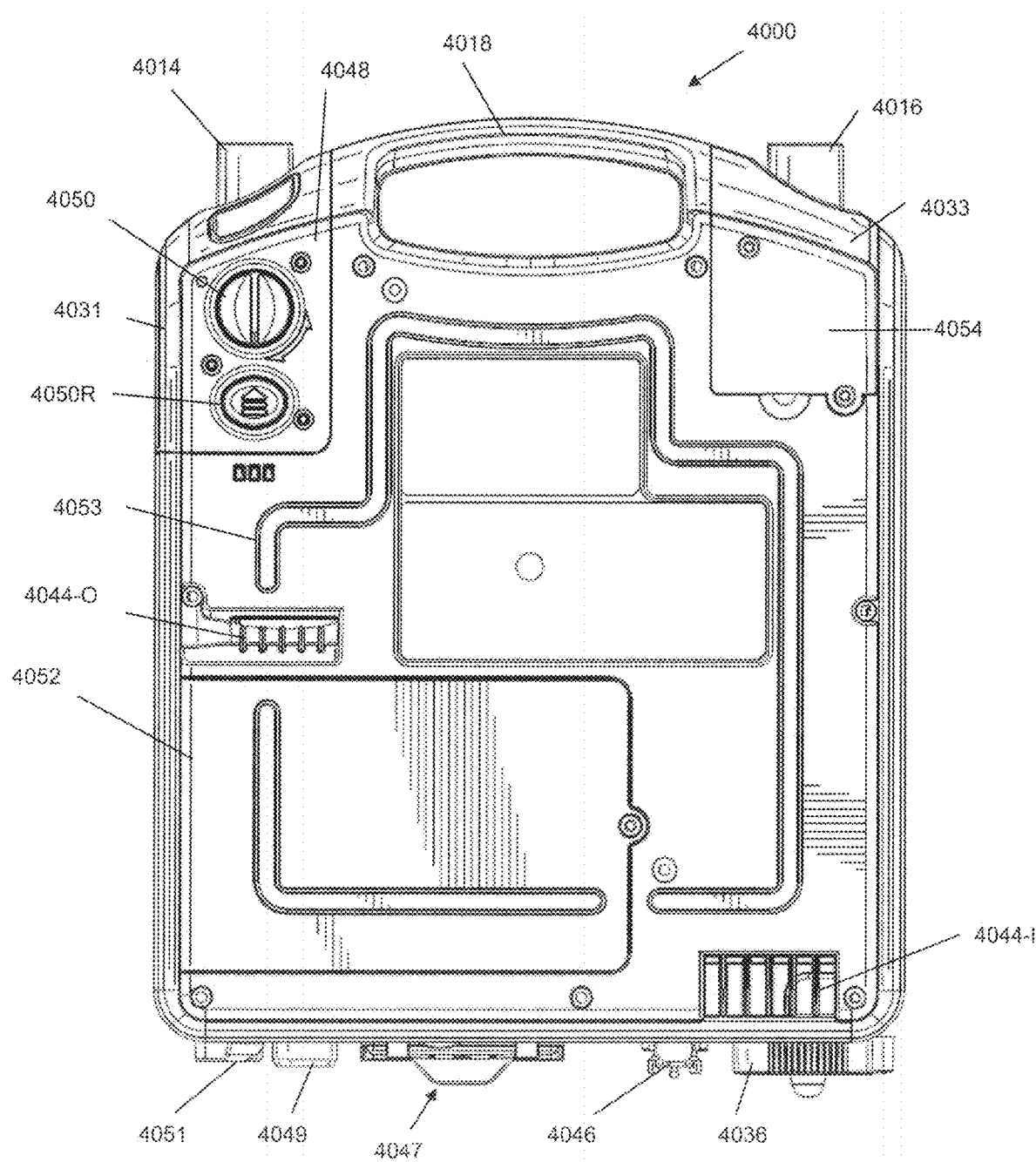

FIG. 4d shows a bottom view of the ventilator device of FIG. 4a.

Figure 4E:
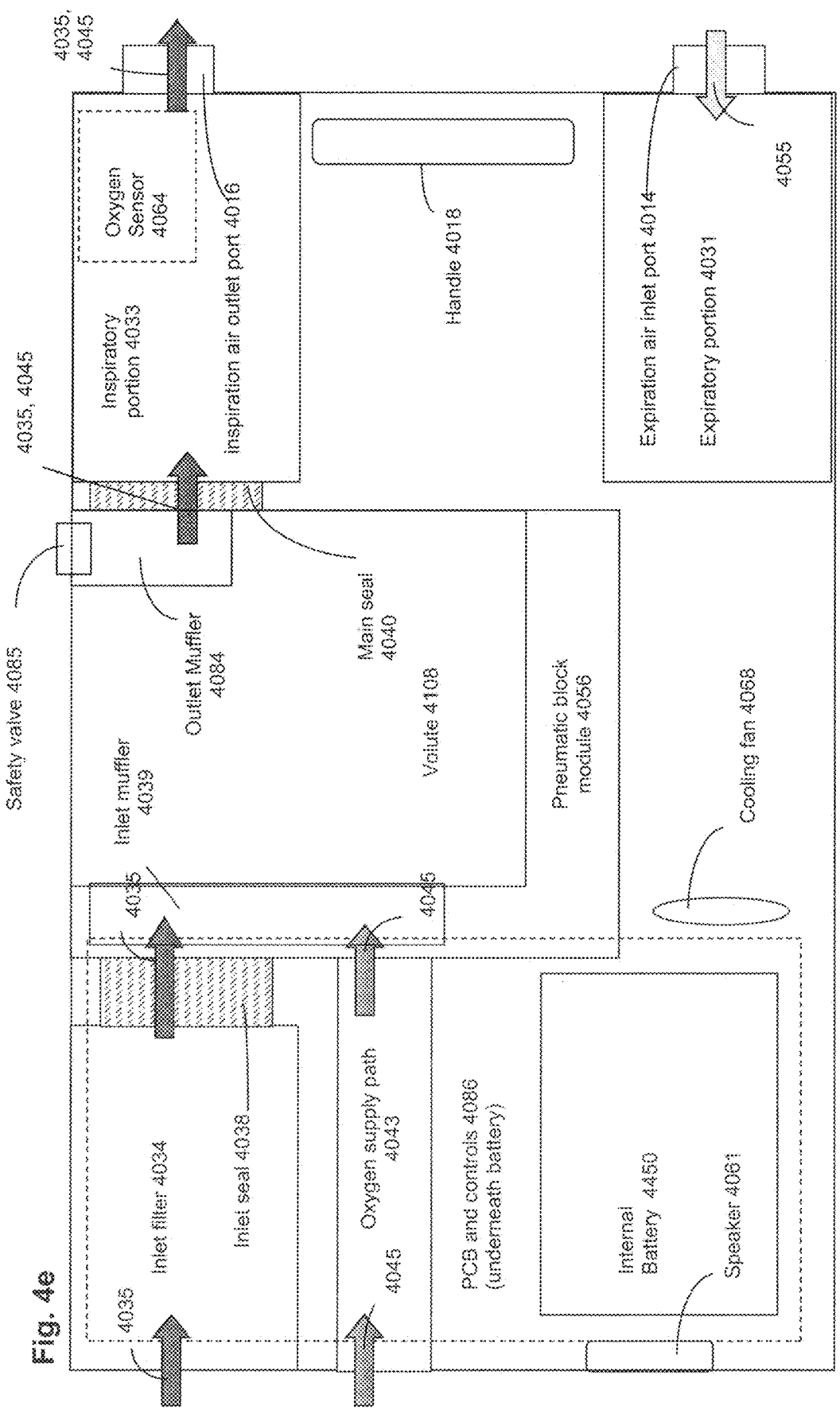

FIG. 4e shows a schematic of the arrangement of internal components in a ventilator according to an aspect of the present technology.

Figure 4F:
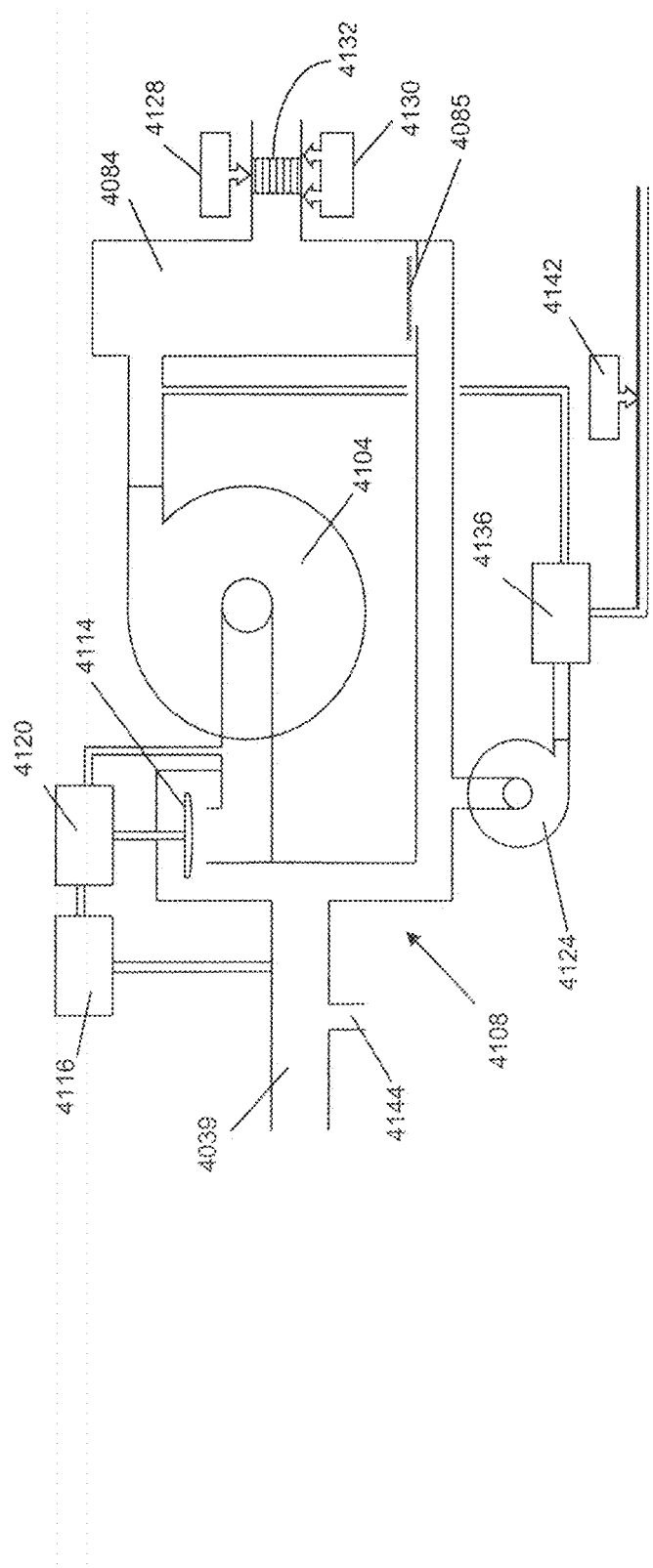

FIG. 4f shows a schematic view of the internals of the pneumatic block according to an aspect of the present technology.

Figure 4G:
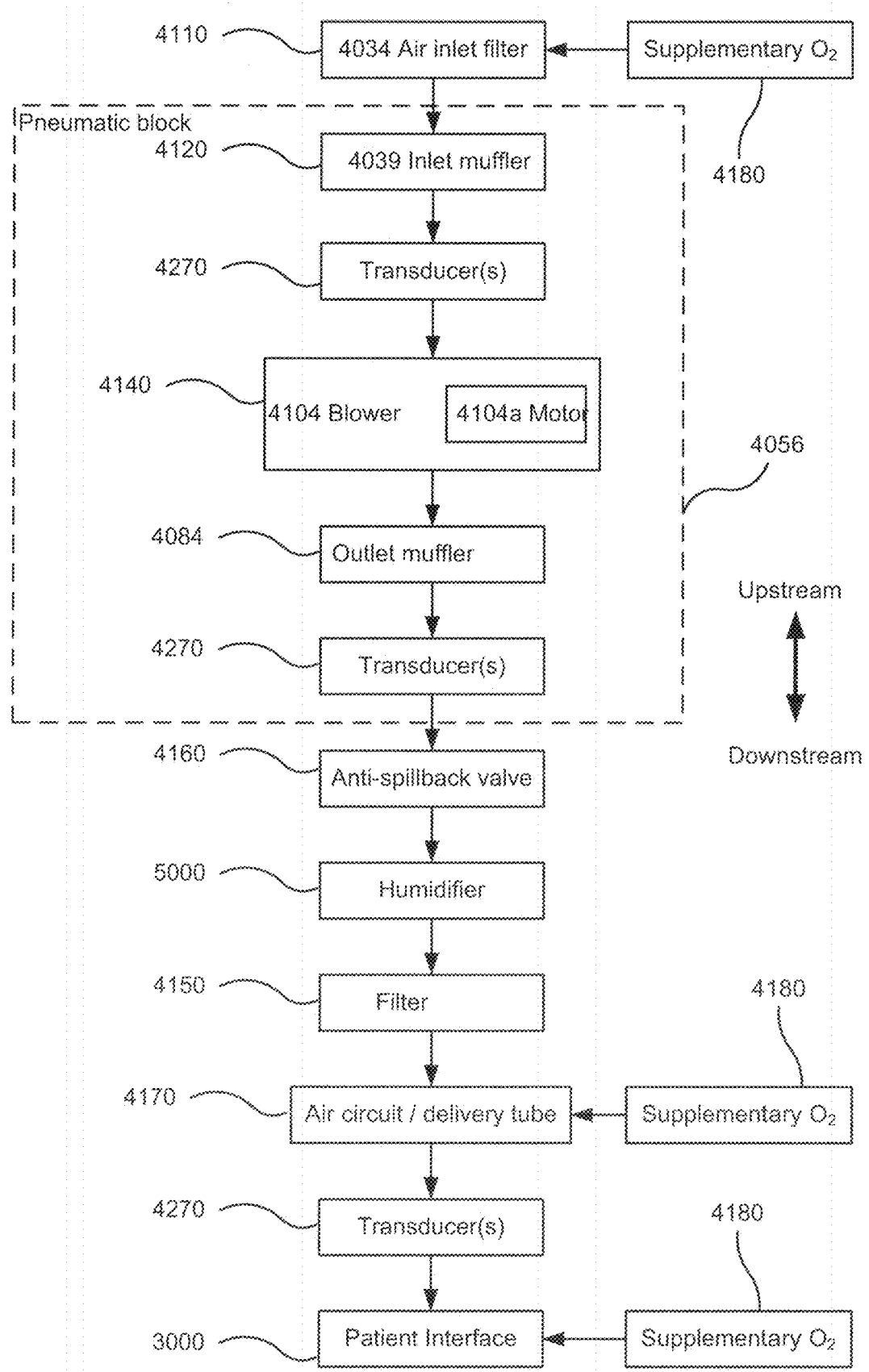

FIG. 4g shows a schematic diagram of the pneumatic circuit of a device in accordance with one form of the present technology. The directions of upstream and downstream are indicated.

Figure 4H:
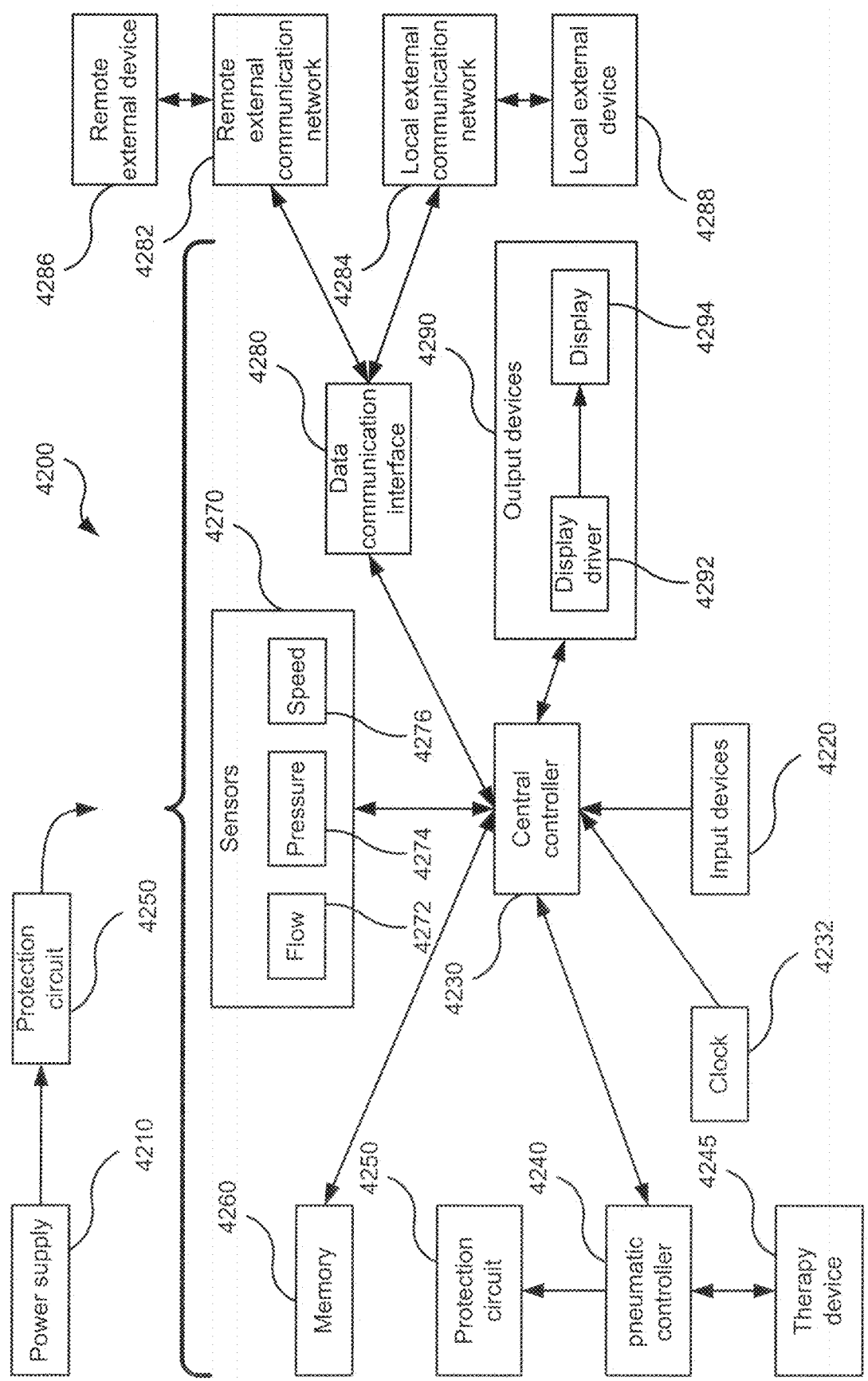

FIG. 4h shows a schematic diagram of the electrical components of a device in accordance with one aspect of the present technology.

Figure 4I:
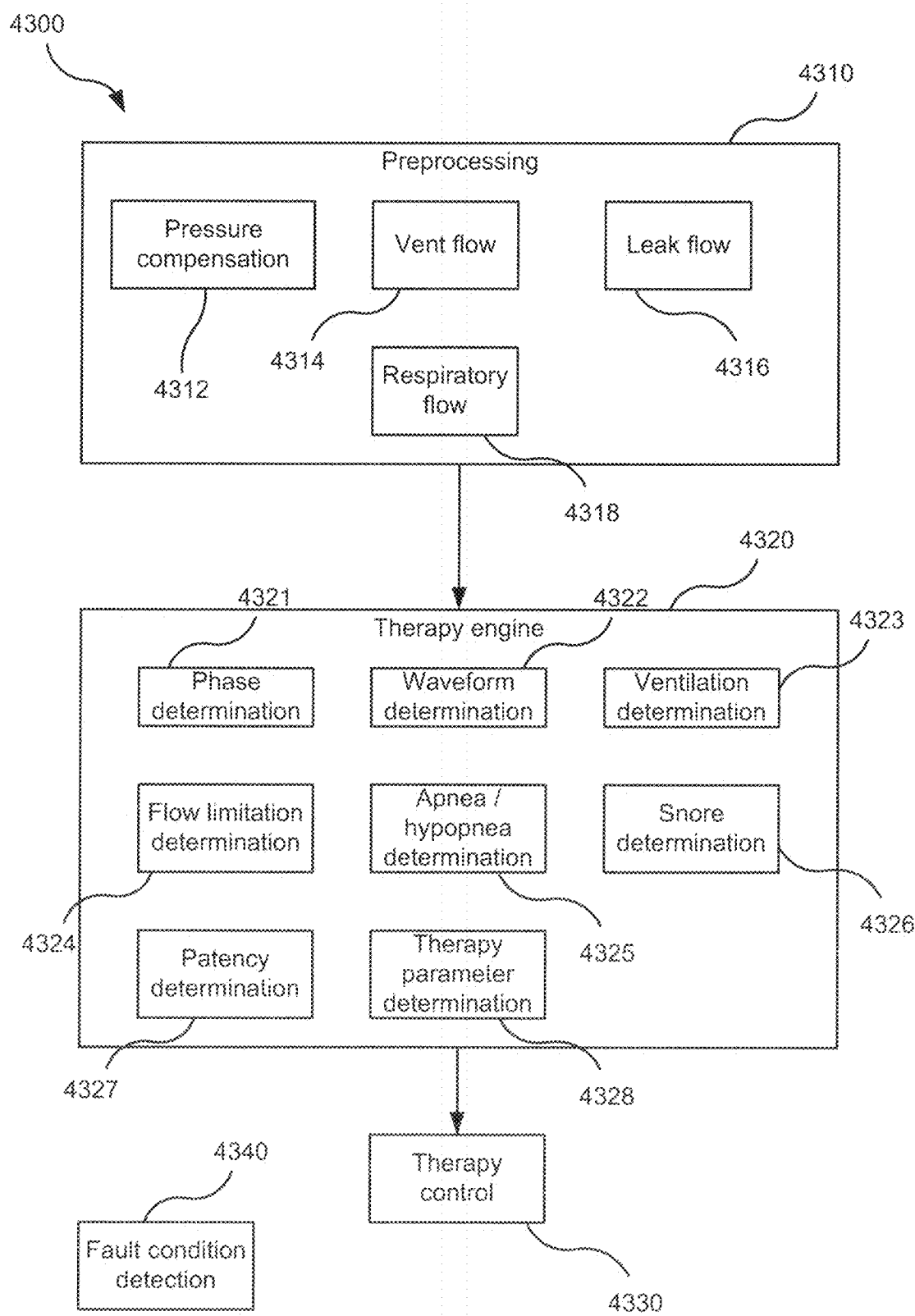

FIG. 4i shows a schematic diagram of the algorithms implemented in a device in accordance with an aspect of the present technology. In this figure, arrows with solid lines indicate an actual flow of information, for example via an electronic signal.

Figure 4J:
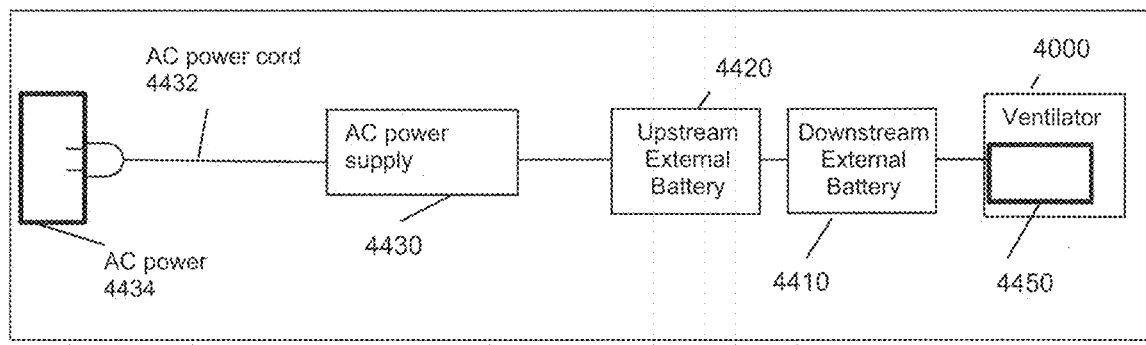

FIG. 4j shows a schematic diagram of the power arrangements for a ventilator provided with AC power according to an aspect of the present technology.

Figure 4K:
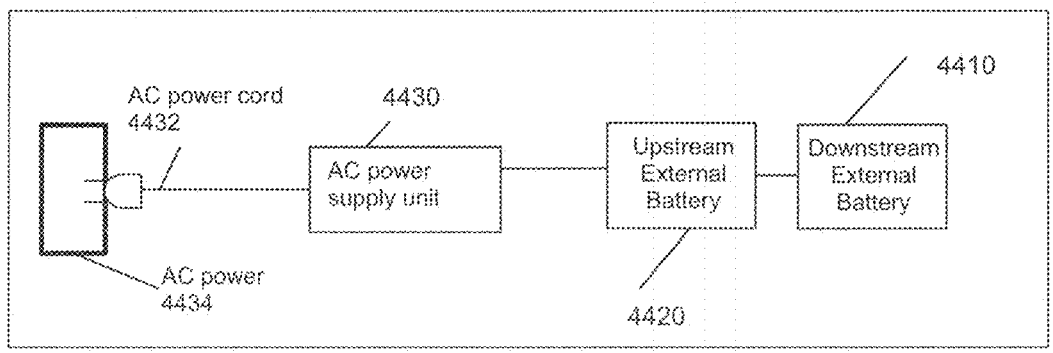

FIG. 4k shows a schematic diagram of the power arrangements for recharging external batteries for a ventilator provided with AC power independent of the ventilator according to an aspect of the present technology.

Figure 4L:
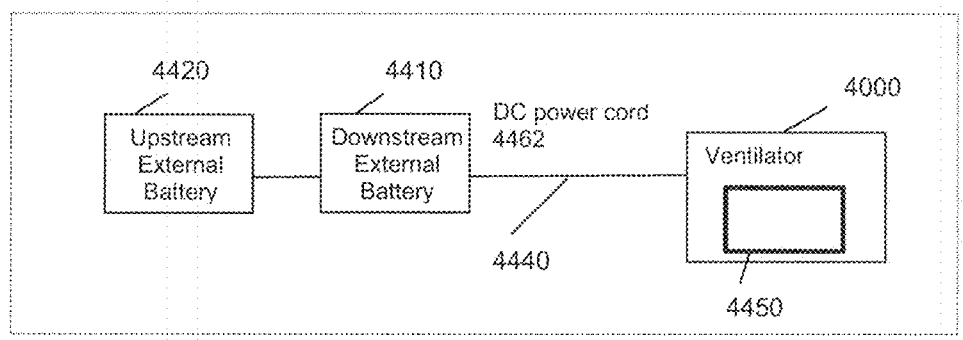

FIG. 4l shows a schematic diagram of the power arrangements for a ventilator provided with external battery power according to an aspect of the present technology.

Figure 4M:
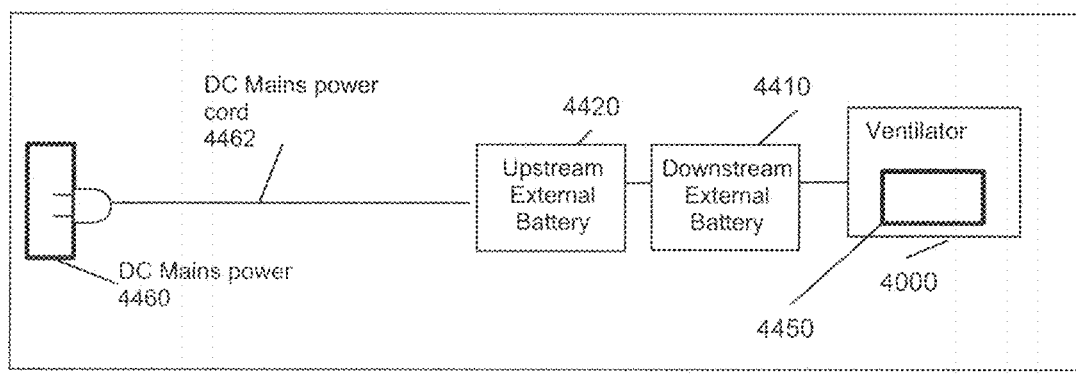

FIG. 4m shows a schematic diagram of the power arrangements for a ventilator provided with DC power according to an aspect of the present technology.

Figure 4N:
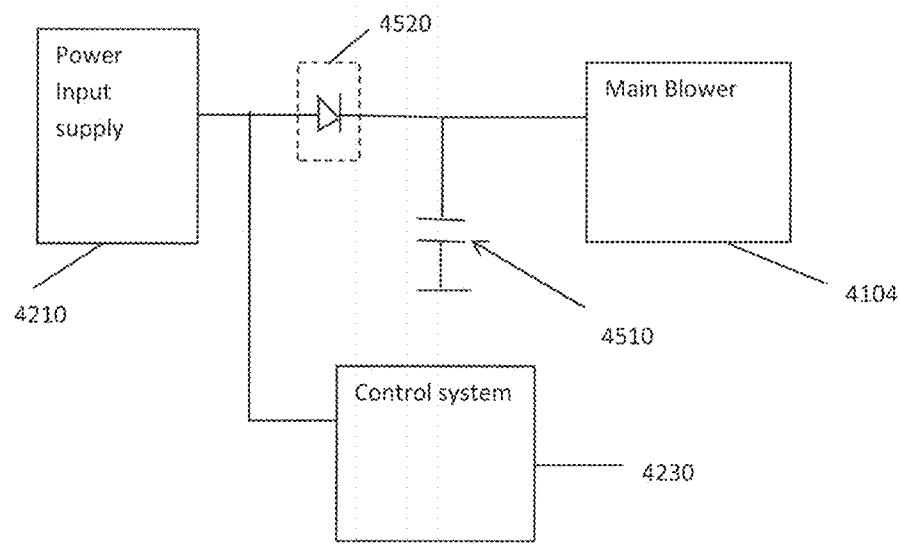

FIG. 4n shows a schematic of a power regeneration circuit according to an aspect of the present technology.

Figure 4O:
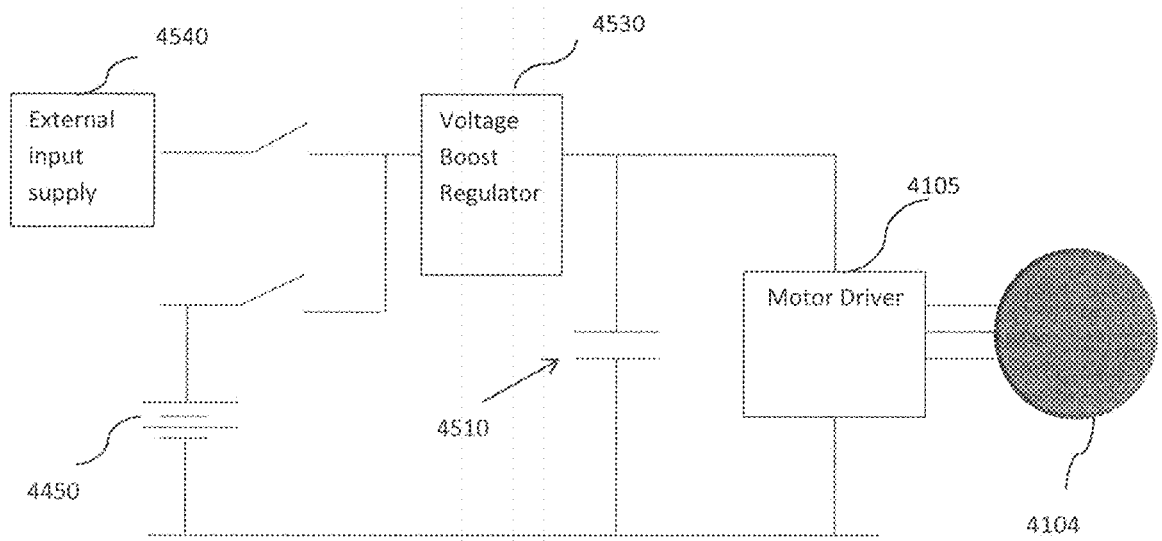

FIG. 4o shows a schematic of a power regeneration circuit including a voltage regulator boost according to another aspect of the present technology.

Figure 4P:
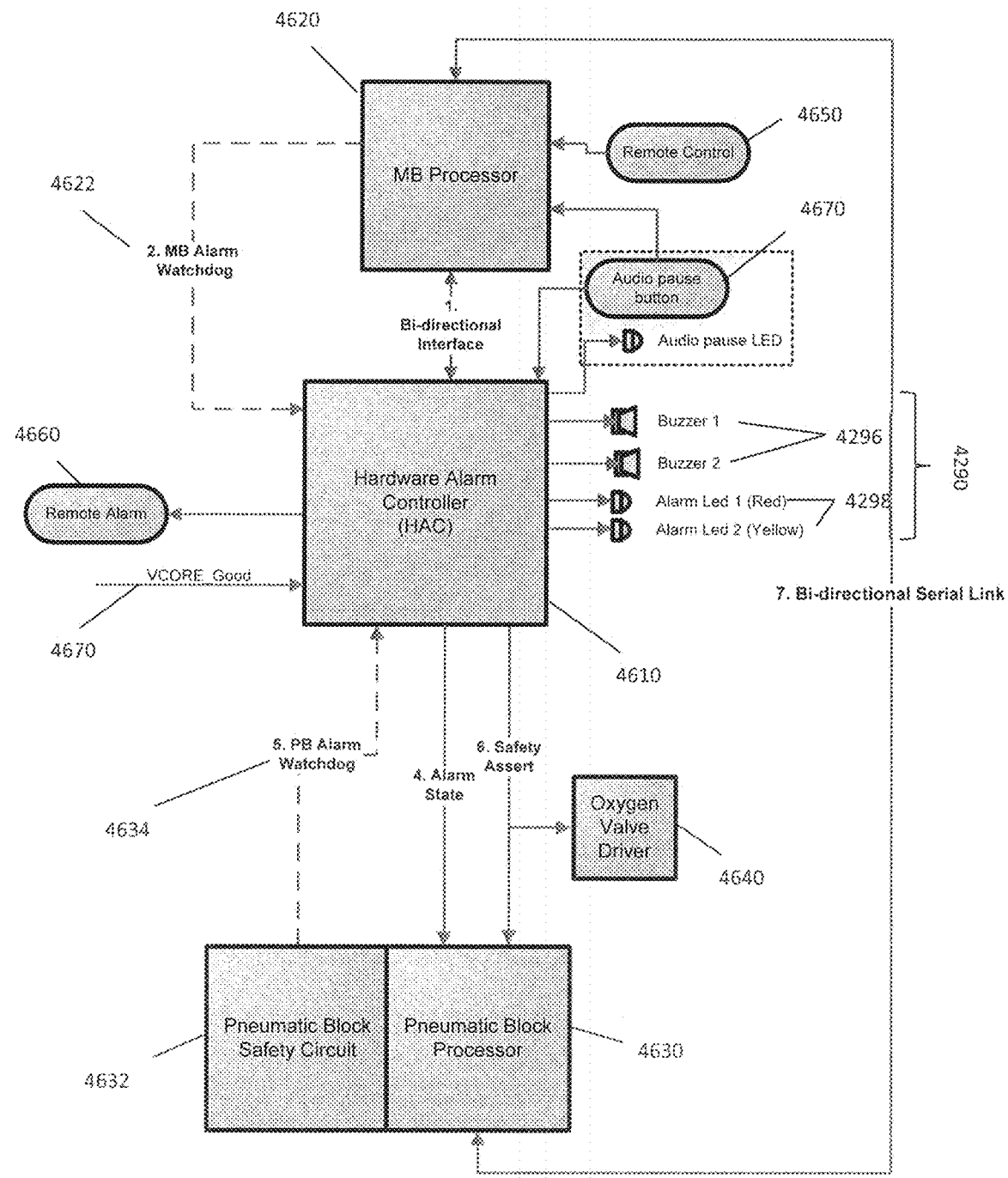

FIG. 4p is a schematic diagram of a hardware alarm controller control system according to another form or example of the present technology.

5.5 Humidifier

FIG. 5 shows a schematic of a humidifier in accordance with one aspect of the present technology.

5.6 Breathing Waveforms

Figure 6A:
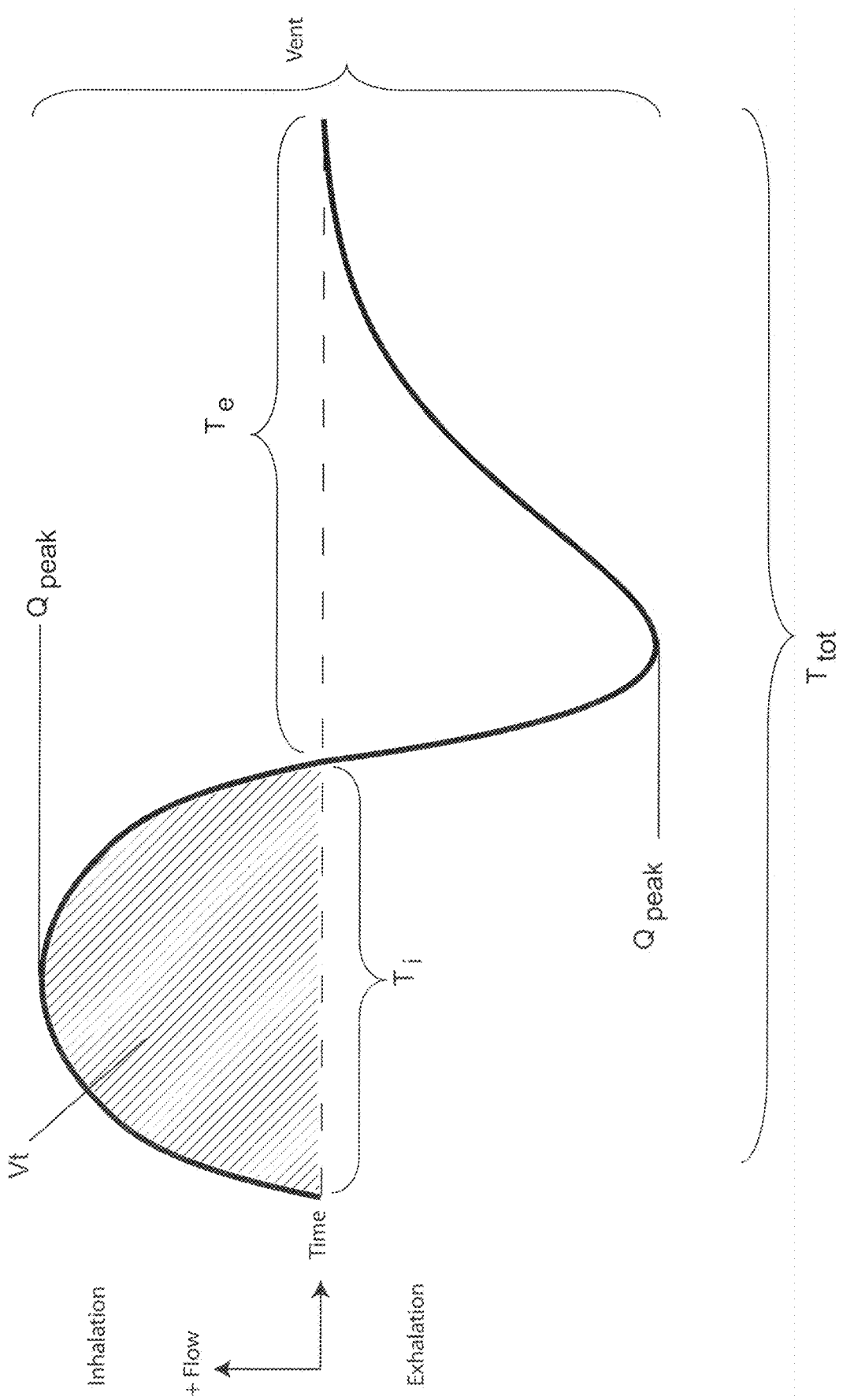

FIG. 6a shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

6 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

6.1 Treatment Systems

In one form, the present technology comprises apparatus for treating a respiratory disorder. The apparatus may comprise a flow generator or blower for supplying pressurised respiratory gas, such as air, to the patient 1000 via an air delivery tube 4170 leading to a patient interface 3000.

6.2 Therapy

In one form, the present technology comprises a method for treating a respiratory disorder comprising the step of applying positive pressure to the entrance of the airways of a patient 1000. In another form of the present technology comprises a method for treating a respiratory disorder comprising the step of applying positive pressure to provide invasive ventilation to an intubated patient. In another form of the present technology provides a method for treating a respiratory disorder comprising the step of providing a pressure-cycled or volume-cycled therapy

6.3 Patient Interface 3000

A non-invasive patient interface 3000 in accordance with one aspect of the present technology comprises the following functional aspects: a seal-forming structure 3100, a plenum chamber 3200, a positioning and stabilising structure 3300 and a connection port 3600 for connection to air circuit 4170.

In one form of the present technology, a seal-forming structure 3100 provides a sealing-forming surface, and may additionally provide a cushioning function. A seal-forming structure 3100 in accordance with the present technology may be constructed from a soft, flexible, resilient material such as silicone.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways. Preferably the plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. Preferably the seal-forming structure 3100 extends in use about the entire perimeter of the plenum chamber 3200.

Preferably the seal-forming portion 3100 of the patient interface 3000 of the present technology is held in sealing position in use by the positioning and stabilising structure 3300, such as headgear.

In one form, the patient interface 3000 includes a vent 3400 constructed and arranged to allow for the washout of exhaled carbon dioxide. One form of vent 3400 in accordance with the present technology comprises a plurality of holes, for example, about 20 to about 80 holes, or about 40 to about 60 holes, or about 45 to about 55 holes. Preferably the vent 3400 is located in the plenum chamber 3200. In one form the patient interface 3000 may also include at least one decoupling structure 3500, for example a swivel or a ball and socket. The vent 3400 may be located in the decoupling structure 3500. Connection port 3600 allows for connection to the air circuit 4170.

The patient interface 3000 may further include a forehead support 3700. The patient interface may also include an anti-asphyxia valve.

In one form of the present technology, a patient interface 3000 includes one or more ports that allow access to the volume within the plenum chamber 3200. In one form this allows a clinician to supply supplemental oxygen. In one form this allows for the direct measurement of a property of gases within the plenum chamber 3200, such as the pressure.

6.4 Device 4000

A ventilator device 4000 in accordance with one form of the present technology is shown in FIGS. 4a to 4e. The ventilator 4000 includes a housing 4012, an expiration air inlet port 4014 and an inspiration outlet port 4016. The ports 4014 and 4016 are connectable to tubes (not shown) which may be inserted into the trachea of a patient, to a face or nasal mask that fits over the nose or mouth or both of a patient, or otherwise attaches to the patient to assist with breathing. The housing for the ventilator may be portable and include a handle 4018 for carrying the ventilator. The housing may have an upper housing case 4020, a chassis 4021 and a lower housing case 4022 that are coupled together to form the external faces of the ventilator. However, it is to be understood that the housing may have other configurations such as only comprising two component parts with an upper and lower casing or may have more than three component parts. The ventilator may include a ventilator or aspects of a ventilator as described the Assignees co-pending U.S. patent application Ser. No. 13/624,167 filed 21 Sep. 2012 and incorporated herein in its entirety.

The chassis 4021 may provide the structural skeleton for the ventilator assembly. The chassis 4021 may be structured to receive an inlet filter assembly 4036 and inlet seal 4038 respectively described in more detail below. The inlet seal 4038 is also configured to couple to an inlet of a pneumatic block module 4056. Preferably the inlet seal 38 is formed of a compliant material such as silicone, the inlet seal may be over moulded onto the inlet of the pneumatic block module 4056.

The chassis 4021 may also comprise a pneumatic block seat into which the pneumatic block module 4056 is located for ease of alignment and assembly of the pneumatic block module 4056 within the housing. The chassis 4021 also may include a portion of the handle 4018.

The rear of the chassis 4021 may include a range of interfaces for a variety of connections and switches on the rear panel. For example, interfaces for electrical connectors 4049, switches 4051, data connections 4047 and oxygen connections 4046.

The chassis 4021 may also provide a number of interfaces to locate and retain components of the ventilator 4000 such as a cooling fan 4068, PCB 4086, and components of an expiratory portion 4031 that is located adjacent the expiration air inlet port 4014 (see FIG. 4e).

The expiratory portion 4031 of the ventilator 4000 is configured to allow the insertion of an expiratory interface module to receive the expired gas from the patient, via the expiration air inlet port 4014. The different expiratory interface modules may include an expiratory valve and an expiratory adaptor.

As seen in FIGS. 4a to 4e the ventilator 4000 may include a battery compartment to locate and interface with a removable internal battery 4450. A removable battery cover 4052 is provided on the outer bottom surface of the lower housing 4022 to allow access to insert or remove the battery. A removable expiratory cover 4048, an oxygen sensor cover 4054 and grills 4044 to allow component heat venting are also provided on the outer bottom surface as seen in FIG. 4d. The lower housing 4022 may also include an anti-slip foot or grip surface or one or more anti-slip or grip feet 4053, such as a thermoplastic polyurethane (TPU) foot, on the outer bottom surface to prevent the ventilator 4000 from slipping off a smooth surface. The anti-slip or grip feet 4053 may also raise the ventilator 4000 to prevent spilt water from pooling under the bottom of the ventilator. A portion of the handle 4018 is also located within the lower housing case 4022.

As seen in FIG. 4a the upper housing case 4020 provides the top face of the ventilator 4000 and is structured to receive a user interface display device 4024. The housing may include a computer or processor driven user interface display device 4024, such as a liquid crystal display (LCD) adapted to receive touch inputs for the computer. The display device may be flush with a top surface of the housing to be easily visible while the ventilator is in use. An alarm indicator light bar 4026, such as a light emitting diode (LED) light bar, and a button 4028 for disabling an audio or visual alarm may be adjacent the display. However it is to be understood that other known user interface systems may be used such as screens, buttons, dial, keys or combinations thereof. The chassis 4021, lower housing case 4022 and upper housing case 4020 are coupled together for assembly of the complete ventilator housing 4012. Fasteners such as screws may be used to assembly the housing 4012 although any other known fasteners may also be used. The chassis 4021 is assembled between the upper housing case 4020 and the lower housing case 4022.

As shown in FIG. 4c, the rear of the housing 4012 may include a filter assembly 4036. Air to be pumped into the lungs of the patient is drawn into the air inlet associated with the filter assembly. The air passes through a permeable filter membrane in the filter and enters an air passage for air flowing to the patient.

The rear of the housing may include data connections 4047 for communications with digital devices such as computer networks, alarm systems, a pulse oximeter (e.g., spO2) and digital recording media. An electrical power connection 4049 and an on-off switch 4051 may also be positioned at the rear of the housing. An input grill 4044-I provides an inlet for air to cool components and permit dissipation of the heat generated by operation of the internal components (e.g., blower motors and CPU). Movement of the heated air across internal components may be driven by a cooling fan 4068 in the housing, which may be near a heated air output grill 4044-O (shown on bottom of housing in FIG. 4d). In addition, an oxygen ($O_2$) inlet port 4046 may be at the rear of the housing, which permits coupling with an oxygen source.

FIG. 4d shows a bottom of the ventilator 4000. The removable expiratory cover 4048, which serves as an external access hatch, provides access to and protection for the compartment of the expiratory portion or section of the housing. Removing the expiratory cover 4048 provides access to any inserted expiratory gas routing module as well as the expiration air inlet port 4014. It also allows for easy removal and replacement of the expiratory gas routing module such as an expiratory valve or expiratory adapter. The expiratory cover 4048 may be tightened to the housing to reduce excess play by a latch 4050 that may be turned with the fingers. Optionally, in some embodiments, the latch might serve to lock the latch from releasing. An optional latch release button 4050R may be operated to disengage the expiratory cover. The release button 4050R may be depressed to unlatch the expiratory cover 4048. A skilled addressee would understand that alternative ways of removably securing and coupling the expiratory cover 4048 to the housing may also be utilized. The bottom of the ventilator housing may also have removable battery cover 4052 for a replaceable internal battery and an oxygen sensor cover 4054 which may be removed to access an oxygen sensor 4047.

FIG. 4e shows the internal components of the ventilator 4000 according to an aspect of the present technology. The ventilator 4000 may include some or all of the following components: an inlet filter 4034, inlet seal 4038, inlet muffler 4039, an oxygen supply path 4043, a pneumatic block module 4056, an inspiratory portion 4033, safety valve 4085, an expiratory portion 4031, PCB and controls 4086, cooling fan 4068 and internal battery 4450.

The pneumatic block module 4056 is arranged within the ventilator such that its air passages are aligned with the filter assembly 4036 at the air inlet 4034, the inspiration outlet port 4016 and the oxygen supply path 4043. Arrows indicate the path of the air flow 4035 and the oxygen flow 4045 respectively through the ventilator 4000. The air flow 4035 enters via the air inlet 4034 and travels through the filter assembly 4036 and inlet seal 4038 into an inlet muffler 4039 of the pneumatic block module 4056. Optionally an oxygen source may be attached at the oxygen inlet port 4046 and the oxygen flow 4045 is directed through the oxygen supply path 4043 and an oxygen seal into the pneumatic block module 4056 where it is combined with the inlet air flow 4035 within the inlet muffler 4039. Within the pneumatic block module 4056 the air flow 4035 is pressurized by a main blower 4104 (see FIG. 40. The pressurized air/oxygen flow 4035, 4045 are directed out of the pneumatic block module 4056 via outlet muffler 4084 and through the main seal 4040 into the inspiratory portion 4033 and then out the inspiration outlet port 4016 to be delivered to the patient interface (not shown) via an air delivery conduit (not shown).

An oxygen sensor 4064, which may be located in an oxygen sensor compartment of the inspiratory portion 4033, measures the amount of oxygen being delivered to patient. The oxygen sensor 4064 may be mounted in the housing 4012 such that it is easily replaced and adjacent the inspiration outlet port 4016. The oxygen sensor detects the oxygen level of the air being pumped to the patient. Data from the oxygen sensor may be used to trigger alarms related to oxygen concentration and to provide data to the microprocessor to display the oxygen concentration on the user interface. The amount of oxygen supplied may be controlled by adjusting the known volumes of air and oxygen supplied to the patient. However, the oxygen sensor may also optionally be used to regulate the amount of supplemental oxygen to be supplied through the oxygen inlet port 4046.

An oxygen sensor cover 4054 (shown in FIG. 4d) on the bottom of the housing is removable to provide access to the oxygen sensor contained within an oxygen sensor compartment of the housing. The oxygen sensor fits in a mount within the housing and adjacent to the inspiration outlet port 4016. A portion of the air flowing through the inspiration outlet port 4016 is sensed by the oxygen sensor. The sensor generates data signals indicating the oxygen level of the gas. The data is conveyed to a data connection which conveys the data to a processor. The processor analyzes the data to determine the amount of supplemental oxygen to be added to the air being pumped to the patient.

The oxygen source may be a low pressure oxygen supply or a high pressure oxygen supply. For the supply of a high pressure oxygen source an oxygen regulator (not shown) may be located within the oxygen supply path 4043 to reduce the pressure from the high pressure oxygen source before the oxygen enters the inlet muffler 4039. The oxygen inlet port 4046 may be adapted to couple to a range of different oxygen connection adaptors to allow the connection of different types of oxygen connectors used in different jurisdictions including but not limited to male or female diameter index safety system (DISS), sleeve indexing system (SIS), National Institute of Standards Technology (NIST) and Association Francaise De Normalisation (AFNOR).

In an alternative arrangement (not shown) a high pressure oxygen source may be provided after the main blower 4104 such as within the outlet muffler 4084 where it is mixed with the pressurized air source. In some examples the high pressure oxygen may be used to provide the pressure source for the gas flow to the patient. In some arrangements low pressure oxygen may optionally be provided to the air circuit 4170 or the patient interface 3000.

Although the pneumatic block module 4056 is schematically shown as a rectangular shape it is to be understood that the pneumatic block module 4056 may have any shape including a non-symmetrical shape that conforms to a seat in the housing and would minimize the possibility that the pneumatic block module 4056 is improperly inserted into the housing.

The main printed circuit board (PCB) 4086, may be assembled and mounted to the chassis 4021 and located between the chassis 4021 and the lower housing case 4022. The electronic components of the main board may include a processor, electrical connectors to convey data signals from the pneumatic block module 4056 such as an electrical power and data connector for the blower which provides pressurized air to the inspiration outlet port 4016. In this regard, the electrical connectors provide power and signal paths between the electronic components on a PCB in the pneumatic block module 4056 and the electronic components on the main PCB in the housing. The electronic components of the main board may also include a data and power connector for any sensors, such as the oxygen sensor 4064. The electronic components in the housing may control a generation of images for the display device, sound signals for a speaker 4061, such as for producing audible alarms, detect signals from pressure and oxygen sensors, and control the rotational speed of the blower. The ventilator 400 may optional include a clock connected to the PCB 4086.

The chassis 4021 may include a plurality of mounting seats or compartments configured to receive different components of the ventilator 4000, such as a pneumatic block mounting seat that may conform to the perimeter of the pneumatic block module 4056, a filter seat and/or a compartment for the inlet filter assembly 4036, and other mounting seats for the low pressure oxygen connection assembly, a cooling fan 4068, and deformable seals. The chassis 4021 may also include embedded or integrated air passages and ports that may be molded within the chassis structure such as for conveying air between sections or compartments of the chassis. For example, air at a known pressure may be channelled through passages of the chassis from the pneumatic block module to the PEEP air supply.

FIG. 4f is a schematic of the internal components of the pneumatic block module 4056. The pneumatic block module 4056 includes the main blower 4104 with volute assembly 4108, an inlet non-return valve assembly 4114, an optional oxygen inlet port 4144, a positive end expiratory pressure (PEEP) blower 4124, outlet muffler 4084, safety valve 4085, pressure sensor 4128, flow sensor 4130 and flow element 4132 and a PEEP pressure sensor 4142. The volute assembly 4108 forms the majority of the air path and performs some of the critical functions of the pneumatic block module 4056.

The pneumatic block 4056 may include electrovalve 4116 and a flow control electrovalve 4120 that are configured to communicate with and control the non-return valve assembly 4114. A PEEP electrovalve 4136 is configured to communicate with the PEEP blower 4124 to control the supply of the pressure from the PEEP blower 4124 to the expiratory portion 4031. A PEEP pressure tube is coupled between the PEEP expiratory valve and a PEEP supply port in the expiratory portion 4031 to provide the PEEP pressure source. The PEEP pressure sensor 4142 senses the PEEP pressure.

FIG. 4g shows a schematic arrangement for another form of a device 4000. The pneumatic path of the device 4000 preferably comprises an inlet air filter 4034, an inlet muffler 4039, a controllable source pressure device 4140 capable of supplying air at positive pressure (preferably a main blower 4104), and an outlet muffler 4084. One or more transducers or sensors 4270, such as pressure sensors 4128 and flow sensors 4130 are included in the pneumatic path.

The preferred pneumatic block 4056 comprises a portion of the pneumatic path that is located within the external housing 4012.

The device 4000 preferably has an electrical power supply 4210, one or more input devices 4220, a central controller 4230, a pneumatic controller 4240, a therapy device 4245, one or more protection circuits 4250, memory 4260, transducers 4270, data communication interface 4280 and one or more output devices 4290. Electrical components 4200 may be mounted on a single Printed Circuit Board Assembly (PCBA). In an alternative form, the device 4000 may include more than one PCBA.

The central controller 4230 of the device 4000 is programmed to execute a set 4300 of one or more algorithm modules in use, preferably including a pre-processing transducer signals module 4310, a therapy engine module 4320, a pressure control module 4330, and further preferably a fault condition module 4340.

6.4.1 Device Mechanical & Pneumatic Components 6.4.1.1 Air Filter(s) 4110

A device in accordance with one form of the present technology may include an air filter 4110, or a plurality of air filters 4110.

In one form, an inlet air filter 4034 is located at the beginning of the pneumatic path upstream of a blower 4104. See FIG. 4g.

In one form, an outlet air filter 4150, for example an antibacterial filter, is located between an outlet of the pneumatic block 4056 and a patient interface 3000. See FIG. 4g.

6.4.1.2 Muffler(s) 4120

In one form of the present technology, an inlet muffler 4039 is located in the pneumatic path upstream of a blower 4104. See FIG. 4g.

In one form of the present technology, an outlet muffler 4084 is located in the pneumatic path between the blower 4104 and a patient interface 3000. See FIG. 4g.

6.4.1.3 Pressure Device 4140

In a preferred form of the present technology, a pressure device 4140 for producing a flow of air at positive pressure is a controllable main blower 4104. For example the main blower may include a brushless DC motor 4404a with one or more impellers housed in a volute. The blower may be preferably capable of delivering a supply of air, for example between about 10 litres/minute and about 120 litres/minute, at a positive pressure in a range from about 3 $cmH_2O$ to about 40 $cmH_2O$, or in other forms up to about 60 $cmH_2O$.

The pressure device 4140 is under the control of the pneumatic controller 4240.

6.4.1.4 Transducer(s) 4270

In one form of the present technology, one or more transducers or sensors 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000. The one or more transducers 4270 may include for example pressure, flow, speed or oxygen sensors.

6.4.1.5 Anti-Spill Back Valve 4160

In one form of the present technology, an anti-spill back valve is located between an optional humidifier 5000 and the device 4000. The anti-spill back valve is constructed and arranged to reduce the risk that water will flow upstream from the humidifier 5000, for example to the motor 4104.

6.4.1.6 Air Circuit 4170

An air circuit 4170 in accordance with an aspect of the present technology is constructed and arranged to allow a flow of air or breathable gasses between an outlet of the device 4000, such as the inspiration air outlet port 4016, and the patient interface 3000. The air delivery circuit 4170 may include a single limb circuit or a double limb circuit. A double limb circuit includes an expiratory conduit for delivery of the patient's expired gas back to the ventilator and out an exhaust port. The exhaust port may include a filter such as an anti-bacterial filter

6.4.1.7 Oxygen Delivery 4180

In one form of the present technology, supplemental oxygen 4180 is delivered to a point in the pneumatic path.

In one form of the present technology, supplemental oxygen 4180 is delivered upstream of the pneumatic block 4056.

In one form of the present technology, supplemental oxygen 4180 is delivered to the air circuit 4170.

In one form of the present technology, supplemental oxygen 4180 is delivered to the patient interface 3000.

6.4.2 Device Electrical Components 4200

6.4.2.1 Power Supply 4210

Power supply 4210 supplies power to the other components of the basic device 4000: the input device 4220, the central controller 4230, the therapy device 4245, and the output device 4290.

In one form of the present technology, the power supply 4210 may include an internal power supply, such as an internal battery 4450 (see FIG. 4j) that may be removably located within the external housing 4012 of the device 4000. The internal battery 4450 may be a lithium-ion battery and may be configured to provide 4-12 hours of use, for example up to 4, 5, 6, 7 or 8 hours of continuous use. The internal battery 4450 may provide a voltage in the range of 10-18 volts direct current (DC) power, such as 12-16.8 volts DC power and have a capacity of 90-100 Watts (W) per hour (hr), such as approximately 95 Watts per hour.

In another form of the present technology, power supply 4210 may alternatively or additionally include one or more external power supplies, such as external batteries 4410, 4420, configured to connect via an electrical cord to a power source connection of the device 4000 (see FIGS. 4j-4m). A plurality of external batteries may be connected in series to the device or ventilator 4000, for example 2, 3, 4 or more external batteries may be connected in series to the device 4000. The external batteries 4410, 4420 may be connected to the device or ventilator 4000 and each other via electrical cables, such as DC cable or power cords 4462. FIGS. 4l to 4m show a downstream external battery 4410 and an upstream external battery 4420 connected in series to the ventilator 4000. It is to be understood that further external batteries (not shown) may be connected in series between the downstream external battery 4410 and the upstream external battery 4420 to extend the available external battery power.

Each external battery includes an input port and output port to allow connection of cables for communication of power and signals along the series. Each of the external batteries 4410, 4420 may be the same or different, i.e. be capable of providing the same amount of power or different amounts of power respectively. An external battery may provide power for 2-12 hours of use, such as up to 4, 5, 6, 7 or 8 hours of continuous use. An external battery 4410, 4420 may provide a voltage in the range of 10-30 volts direct current (DC) power, such as 24-26 volts DC power and have a capacity of 90-100 Watts (W) per hour (hr), such as approximately 95, 96, 97 Watts per hour.

In another arrangement the power supply 4210 allows connection to an Alternating Current (AC) power source via an AC power Supply unit (PSU) 4430 (see FIG. 4j). The AC PSU 4430 may be a switched mode power supply that may provide universal input in a range of between 80-270 volts AC or between 100-240 volts AC. The AC PSU 4430 may provide a power output of 60-100 Watts (W), such as approximately 90 W and a power supply of approximately 24 volts DC power. The AC PSU 4430 may be suitable for use on an aircraft. The AC PSU 4430 may be electrically connected to the power source connection of the ventilator or device 4000 directly (i.e. no external batteries are connected to the ventilator 4000, not shown) or in series upstream from one or external batteries 4410, 4420 that are electrically connected to the ventilator 4000 as shown in FIG. 4j.

In a further arrangement shown in FIG. 4m, the power supply 4210 may allow connection to a DC mains power supply 4460 via a DC mains power cord 4462. The DC mains power supply may provide approximately 12-24 volts of power. The DC mains power cord 4462 may electrically connect between the power source connection of the ventilator or device 4000 and the DC mains power supply 4460 without any intervening external batteries (not shown). Alternatively, as shown in FIG. 4m, one or more of the upstream external battery 4420 and the downstream external battery 4410 may also be connected in series between the ventilator 4000 and the DC mains power. In one arrangement the external batteries 4410, 4420, if connected, will not be charged by the DC power supply when the device is in use. However, alternatively the DC mains power may be used to charge the external batteries 4410, 4420 depending upon the power usage requirements of the device 4000 and the available power being supplied by the DC mains power 4460. The internal battery 4450 may also be present in ventilator 4000 and may optionally be charged by the DC mains power 4460.

It is to be understood that the above power capacity ranges are exemplary only and the AC PSU 4430, the internal battery 4450, and the external batteries 4410, 4420 may have different power capacity and outputs to those described above. The power management of the device 4000 is described in more detail below.

6.4.2.1.1 Input Device(s) 4220

Input devices 4220 comprises buttons, switches or dials to allow a person to interact with the device 4000. The buttons, switches or dials may be physical devices, or software devices accessible via a touch screen. The buttons, switches or dials may, in one form, be physically connected to the external housing 4012, or may, in another form, be in wireless communication with a receiver that is in electrical connection to the central controller 4230.

In one form the input device 4220 may be constructed and arranged to allow a person to select a value and/or a menu option.

6.4.2.1.2 Central Controller 4230

In one form of the present technology, the central controller or Processor 4230 is a dedicated electronic circuit configured to receive input signal(s) from the input device 4220, and to provide output signal(s) to the output device 4290 and/or the therapy device controller 4245.

In one form, the central controller 4230 is an application-specific integrated circuit. In another form, the central controller 4230 comprises discrete electronic components.

The processor 4230 is configured to receive input signal(s) from one or more transducers 4270, and one or more input devices 4220.

The processor 4230 is configured to provide output signal(s) to one or more of an output device 4290, a pneumatic controller 4240, a data communication interface 4280 and humidifier controller 5250.

In some forms of the present technology, the processor 4230, or multiple such processors, is configured to implement the one or more methodologies described herein such as the one or more algorithms 4300 expressed as computer programs stored in a non-transitory computer readable storage medium, such as memory 4260. In some cases, as previously discussed, such processor(s) may be integrated with a device 4000. However, in some forms of the present technology the processor(s) may be implemented discretely from the pressure generation components of the device 4000, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

6.4.2.1.3 Therapy Device 4245

In one form of the present technology, the therapy device 4245 is configured to deliver therapy to a patient 1000 under the control of the central controller 4230.

6.4.2.1.4 Output Device 4290

An output device 4290 in accordance with the present technology may take the form of one or more of a visual, audio, and haptic output. A visual output may be a Liquid Crystal Display (LCD) or Light Emitting Diode (LED) display. An audio output may be a speaker or audio tone emitter.

6.4.2.1.5 Clock 4232

Preferably device 4000 includes a clock 4232 that is connected to processor 4230.

6.4.2.1.6 Pneumatic Controller 4240

In one form of the present technology, the pneumatic controller 4240 is a pressure control module 4330 that forms part of the algorithms 4300 executed by the processor 4230.

In one form of the present technology, pneumatic controller 4240 is a dedicated motor control integrated circuit.

In one form of the present technology, pneumatic controller 4240 is a pneumatic block processor 4630.

6.4.2.1.7 Protection Circuits 4250

Preferably a device 4000 in accordance with the present technology comprises one or more protection circuits 4250.

One form of protection circuit 4250 in accordance with the present technology is pneumatic block safety circuit 4632.

One form of protection circuit 4250 in accordance with the present technology is an electrical protection circuit.

One form of protection circuit 4250 in accordance with the present technology is a temperature or pressure safety circuit.

One form of protection circuit 4250 in accordance with the present technology is an alarm controller. The alarm controller may be a hardware alarm controller 4610 as described in more detail below.

6.4.2.1.8 Memory 4260

In accordance with one form of the present technology the device 4000 includes memory 4260, preferably non-volatile memory. In some forms, memory 4260 may include battery powered static RAM. In some forms, memory 4260 may include volatile RAM.

Preferably memory 4260 is located on PCBA. Memory 4260 may be in the form of EEPROM, or NAND flash.

Additionally or alternatively, device 4000 includes removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

6.4.2.1.9 Transducers 4270

Transducers may be internal of the device, or external of the device. External transducers may be located for example on or form part of the air delivery circuit, e.g. the patient interface. External transducers may be in the form of non-contact sensors such as a Doppler radar movement sensor that transmit or transfer data to the device.

6.4.2.1.9.1 Flow 4272

A flow transducer 4272 in accordance with the present technology may be based on a differential pressure transducer, for example, an SDP600 Series differential pressure transducer from SENSIRION or Zephyr™ flow sensors from HONEYWELL. The differential pressure transducer is in fluid communication with the pneumatic circuit, with one of each of the pressure transducers connected to respective first and second points in a flow restricting element.

In use, a signal representing total flow Qt from the flow transducer 4272 is received by the processor 4230.

6.4.2.1.9.2 Pressure 4274

A pressure transducer 4274 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC. A further alternative suitable pressure transducer is a sensor from the series of TruStability™ pressure sensors from HONEYWELL.

In use, a signal from the pressure transducer 4274 is received by the processor 4230. In one form, the signal from the pressure transducer 4274 is filtered prior to being received by the processor 4230.

6.4.2.1.9.3 Motor Speed 4276

In one form of the present technology a motor speed signal 4276 is generated. A motor speed signal 4276 is preferably provided by pneumatic controller 4240. Motor speed may, for example, be generated by a speed sensor, such as a Hall effect sensor.

6.4.2.1.10 Data Communication Systems 4280

In one preferred form of the present technology, a data communication interface 4280 is provided, and is connected to processor 4230. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor 4230. In another form, data communication interface 4280 is an integrated circuit that is separate from processor 4230.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

6.4.2.1.11 Output Devices Including Optional Display, Alarms 4290

An output device 4290 in accordance with the present technology may take the form of one or more of a visual, audio and haptic unit. A visual display may be a Liquid Crystal Display (LCD) or Light Emitting Diode (LED) 4298 display. An audio display may be a buzzer 4296.

6.4.2.1.11.1 Display Driver 4292

A display driver 4292 receives as an input the characters, symbols, or images intended for display on the display 4294, and converts them to commands that cause the display 4294 to display those characters, symbols, or images.

6.4.2.1.11.2 Display 4294

A display 4294 is configured to visually display characters, symbols, or images in response to commands received from the display driver 4292

6.4.3 Device Algorithms 4300

6.4.3.1 Pre-Processing Module 4310

As illustrated in FIG. 4i, a pre-processing module 4310 in accordance with the present technology receives as an input, raw data from a transducer, for example a flow or pressure transducer, and preferably performs one or more process steps to calculate one or more output values that will be used as an input to another module, for example a therapy engine module 4320.

In one form of the present technology, the output values include the interface or mask pressure Pm, the respiratory flow Qr, and the leak flow Ql.

In various forms of the present technology, the pre-processing module 4310 comprises one or more of the following algorithms: pressure compensation 4312, vent flow 4314, leak flow 4316, respiratory flow 4318, and jamming detection 4319.

6.4.3.1.1 Pressure Compensation 4312

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop in the air circuit 4170 and provides as an output an estimated pressure, Pm, in the patient interface 3000.

6.4.3.1.2 Vent Flow 4314

In one form of the present technology, a vent flow calculation algorithm 4314 receives as an input an estimated pressure, Pm, in the patient interface 3000 and estimates a vent flow of air, Qv, from a vent 3400 in a patient interface 3000.

6.4.3.1.3 Leak Flow 4316

In one form of the present technology, a leak flow algorithm 4316 receives as an input a total flow, Qt, and a vent flow Qv, and provides as an output a leak flow Ql by calculating an average of Qt-Qv over a period sufficiently long to include several breathing cycles, e.g. about 10 seconds.

In one form, the leak flow algorithm 4316 receives as an input a total flow, Qt, a vent flow Qv, and an estimated pressure, Pm, in the patient interface 3000, and provides as an output a leak flow Ql by calculating a leak conductance, and determining a leak flow Ql to be a function of leak conductance and pressure, Pm. Preferably leak conductance is calculated as the quotient of low pass filtered non-vent flow Qt-Qv, and low pass filtered square root of pressure Pm, where the low pass filter time constant has a value sufficiently long to include several breathing cycles, e.g. about 10 seconds.

6.4.3.1.4 Respiratory Flow 4318

In one form of the present technology, a respiratory flow algorithm 4318 receives as an input a total flow, Qt, a vent flow, Qv, and a leak flow, Ql, and estimates a respiratory flow of air, Qr, to the patient, by subtracting the vent flow Qv and the leak flow Ql from the total flow Qt.

6.4.3.2 Therapy Engine Module 4320

In one form of the present technology, a therapy engine module 4320 receives as inputs one or more of a pressure, Pm, in a patient interface 3000, and a respiratory flow of air to a patient, Qr, and provides as an output, one or more therapy parameters.

In one form of the present technology, a therapy parameter is a treatment pressure Pt.

In one form of the present technology, a therapy parameter is one or more of a level of pressure support, and a target ventilation.

6.4.3.2.1 Phase Determination 4321

In one form of the present technology, a phase determination algorithm 4321 receives as an input a signal indicative of respiratory flow, Qr, and provides as an output a phase of a breathing cycle of a patient 1000.

In one form, the phase output is a discrete variable with values of either inhalation or exhalation.

In one form, the phase output is a discrete variable with values of one of inhalation, mid-inspiratory pause, and exhalation.

In one form, the phase output is a continuous variable, for example varying from 0 to 1, or 0 to 2 Pi.

In one form, the phase output is determined to have a discrete value of inhalation when a respiratory flow Qr has a positive value that exceeds a positive threshold. In one form, a phase is determined to have a discrete value of exhalation when a respiratory flow Qr has a negative value that is more negative than a negative threshold.

6.4.3.2.2 Waveform Determination 4322

In one form of the present technology, a control module 4330 controls a therapy device 4245 to provide an approximately constant positive airway pressure throughout a respiratory cycle of a patient.

In one form of the present technology, a control module 4330 controls a therapy device 4245 to provide positive airway pressure according to a predetermined waveform of pressure vs phase. In one form, the waveform is maintained at an approximately constant level for all values of phase. In one form, the waveform is a square wave, having a higher value for some values of phase, and a lower level for other values of phase.

In one form of the present technology a waveform determination algorithm 4322 receives as an input a value indicative of current patient ventilation, Vent, and provides as an output a waveform of pressure vs. phase.

6.4.3.2.3 Ventilation Determination 4323

In one form of the present technology, a ventilation determination algorithm 4323 receives an input a respiratory flow Qr, and determines a measure indicative of patient ventilation, Vent.

In one form ventilation determination algorithm 4323 determines a current value of patient ventilation, Vent, as the half the low-pass filtered absolute value of respiratory flow, Qr.

6.4.3.2.4 Determination of Inspiratory Flow Limitation 4324

In one form of the present technology, a processor executes one or more algorithms for the detection of inspiratory flow limitation.

In one form the algorithm 4324 receives as an input a respiratory flow signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath, similar to the inspiratory portion of the breath shown in FIG. 6a. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by processor 4230 for the preceding several inspiratory events. This is repeated over the same inspiratory events for the second such point, and so on. Thus, for example, sixty five scaled data points are generated by processor 4230, and represent a moving average of the preceding several inspiratory events, e.g. three events. The moving average of continuously updated values of the (e.g. sixty five) points are hereinafter called the "scaled flow", designated as Qs(t). Alternatively, a single inspiratory event can be utilised rather than a moving average.

From the scaled flow, two shape factors relating to the determination of partial obstruction may be calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

The above methods are exemplary and it is to be understood that other methods of determining inspiratory flow limitation may also be used.

6.4.3.2.5 Determination of Apneas and Hypopneas 4325

In one form of the present technology, a processor 4230 executes one or more algorithms for the determination of the presence of apneas and/or hypopneas.

Preferably the one or more algorithms receive as an input a respiratory flow signal Qr and provide as an output a flag that indicates that an apnea or respectively an hypopnea has been detected.

In one form, an apnea will be said to have been detected when a function of respiratory flow Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

The above methods are exemplary and it is to be understood that other methods of determining the occurrence of apneas and/or hypopneas may also be used.

6.4.3.2.6 Determination of Snore 4326

In one form of the present technology, a processor 4230 executes one or more snore algorithms for the detection of snore.

In one form the snore algorithm 4326 receives as an input a respiratory flow signal Qr and provides as an output a metric of the extent to which snoring is present.

Preferably the algorithm 4326 comprises the step of determining the intensity of the flow signal in the range of 30-300 Hz. Further preferably, algorithm 4326 comprises a step of filtering the respiratory flow signal Qr to reduce background noise, e.g. the sound of airflow in the system from the blower.

The above methods are exemplary and it is to be understood that other methods of determining snore may also be used.

6.4.3.2.7 Determination of Airway Patency 4327

In one form of the present technology, a processor 4230 executes one or more algorithms for the determination of airway patency.

In one form, airway patency algorithm 4327 receives as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency algorithm 4327 receives as an input a respiratory flow signal Qr, and determines the presence or absence of a cardiogenic signal. The absence of a cardiogenic signal is taken to be an indication of a closed airway.

6.4.3.2.8 Determination of Treatment Pressure 4328

In one form of the present technology, processor 4230 executes one or more algorithms 4328 for the determination of a target treatment pressure Pt.

Preferably the algorithm 4328 receives as an input one of more of the following:
  i. A measure of respiratory phase;
  ii. A waveform;
  iii. A measure of ventilation;
  iv. A measure of inspiratory flow limitation;
  v. A measure of the presence of apnea and/or hypopnea;
  vi. A measure of the presence of snore; and
  vii. A measure of the patency of the airway.

Pi=phase(time), the phase may be discrete or continuous.
Phi=waveform function(Pi), this wave may include a square wave, sinusoidal or other wave shapes.
Integral controller Amplitude, A=G*Int(Vent−Vtgt)dt. Other forms of controller may be used such as P, PI, PID.

$$Pt(t)=A*\Phi(Pi)+P0.$$

P0="DC" component, may be constant, may be a function of indices or measures of one or more of flow limitation, apnea, hypopnea, patency, and snore.

(Note: In a basic CPAP mode A may be zero, in which case the overall pressure equation simplifies)

The algorithm 4328 determines the treatment pressure Pt as a function of indices or measures of one or more of flow limitation, apnea, hypopnea, patency, and snore. In one implementation, these measures are determined on a single breath basis, rather than on an aggregation of several previous breaths.

6.4.3.3 Control Module 4330

A control module 4330 in accordance with one aspect of the present technology receives as an input a target treatment pressure Pt, and controls a therapy device 4245 to deliver that pressure.

A control module 4330 in accordance with one aspect of the present technology receives as an input an EPAP pressure and an IPAP pressure, and controls a therapy device 4245 to deliver those respective pressures.

6.4.3.4 Detection of Fault Conditions 4340

In one form of the present technology, a processor executes one or more methods for the detection of fault conditions. Preferably the fault conditions detected by the one or more methods includes at least one of the following:
  Power failure (no power, or insufficient power)
  Transducer fault detection
  Failure to detect the presence of a component
  Operating parameters outside recommended ranges (e.g. pressure, flow, temperature, $PaO_2$)
  Failure of a test alarm to generate a detectable alarm signal.

Upon detection of the fault condition, the corresponding algorithm signals the presence of the fault by one or more of the following:
  Initiation of an audible, visual &/or kinetic (e.g. vibrating) alarm
  Sending a message to an external device
  Logging of the incident

6.4.3.5 Therapy Device 4245

In a preferred form of the present technology, the therapy device 4245 is under the control of the control module 4330 to deliver therapy to a patient 1000.

6.5 Humidifier 5000

6.5.1 Humidifier

Optionally in one form of the present technology there is provided a humidifier 5000 comprising a water reservoir 5110 and a heating plate 5120. The water reservoir is structured to contain a supply of liquid, such as water 5140. The heater plate is arranged to heat at least a portion of the supply of liquid 5140 to produce water vapour for uptake into the air flow that passes through the humidifier 5000. The humidifier 500 may include a temperature sensor 5130 to monitor the temperature of the heater plate and optionally additional sensors 5160 such as temperature, relative humidity and/or absolute humidity sensors.

A heated air delivery conduit 4172 may optionally be used to reduce rainout in the air delivery conduit between the humidifier 5000 and the patient interface 3000. The heated air delivery conduit 4172 may be a single limb circuit or a double limb circuit, where one or both of the limbs may be heated. A heating coil 4174 may be provided within the heated conduit 4174 to heat the air flow as it travels through the air delivery conduit 4172. The air delivery conduit 4172 may also optionally include one or more sensors 4176, such as temperature, flow, humidity o pressure sensors.

The humidifier may be coupled between the device 4000 and the patient interface 3000 as shown in FIG. 5. Alternatively the humidifier 5000 may be attached upstream of the device 4000 (not shown). The humidifier 5000 may be a separable component to the device 4000 and be coupled via an air delivery conduit 4170 or arranged to directly connect to the device 4000. In an alternative arrangement the humidifier 5000 may be integrally constructed with the device 4000 (not shown). The humidifier 5000 is configured to humidify the gas prior to delivery to the patient 1000.

The humidifier may use an alternative humidification system such as the CounterStream™ humidification system described in U.S. Pat. No. 7,975,687 the contents of which is incorporated herein in its entirety.

6.6 Power Management

6.6.1 Power Usage and Charging Arrangements

As mentioned above the device or ventilator 4000 includes a power source connection that is configured to connect to a range of different power supply sources: an Alternating Current (AC) power 4434 via an AC power supply unit (PSU) 4430 using an AC power cord 4432, one or more external batteries 4410, 4420, and Direct current (DC) mains power 4460 using a DC power cord 4462. The system may include one or more of these different power supply sources coupled to the ventilator 4000 at one time. The power source may be coupled to the device 4000 in series via the power source connection. The device 4000 may generally only be connected to the AC PSU 4430 or the DC mains power 4460 at any one time. The ventilator or device 400 may also include an internal battery 4450 located within the device as described above that may be used as a power supply source. In use, generally one of the connected power supply sources may be utilised at a time to provide power to the device 4000.

In some arrangements the internal battery 4450 must be present in the device 4000 for ventilation therapy to be provided by the device even if another power source is coupled to the ventilator and being used as the primary source of power. The device 4000 may be able to be turned on but therapy cannot commence in the absence of the internal battery 4450. An alarm may signal the lack of an internal battery 4450. The required presence of the internal battery 4450 is to ensure therapy can be continued if the primary or external power supply is interrupted for some reason, for example during a power cut. The presence of the internal battery 4450 provides a safety backup for the device 4000.

The controller of the ventilator 4000 may detect the connection of the different power supply sources based on the detection of different voltage ranges along the communication signal. The voltage ranges for the different power supply sources do not overlap. The AC PSU 4430 may provide a first voltage range, e.g. 1.3 to 1.8 Volts, the DC mains power 4460 may provide a different second voltage range e.g. 0.05 Volts to 1.2 Volts, and the external battery may provide a third voltage range, e.g. 2.2 to 3 Volts. These voltage ranges are exemplary only and it is to be understood that other voltage ranges may be used provided the voltage ranges do not overlap.

The device includes a power usage priority scheme to ensure that power is used from the different power supply sources in a prioritised manner. The AC PSU 4430 has the highest power priority so will always be used at the primary source of power if attached. Thus, when the AC PSU 4430 is coupled between a main AC power supply and the device 4000, the AC PSU 4430 will have power priority to provide the power supply to the device 4000 irrespective of what other forms of power supply sources are also coupled to the device 4000. If, as shown in FIG. 4*j*, one or more external batteries and an internal battery 4450 are also connected in series then the power provided through the AC PSU 4430 may also be used to recharge the one or more external batteries 4410, 4420 and/or the internal battery 4450 as required whilst also providing the power for running the ventilator 4000. However at all times the running of the ventilator 4000 takes priority over the use of the power supplied and the recharging of any batteries is reduced when more power is required by the ventilator 4000. In some arrangements the AC PSU 4430 may provide power to recharge the batteries when the output power required by the ventilator is below a threshold. The threshold may be the maximum power or close to the maximum power that the AC PSU 4430 can supply, for example 90 Watts. Thus, a dynamic power management system is used to control the recharging of the batteries.

There may be a priority for the recharging scheme, such that when the AC mains power is used for recharging, the internal battery 4450 has the highest priority and is preferably recharged first. The one or more external batteries may be recharged when the internal battery 4450 is substantially fully recharged. The recharge of the one or more external batteries also may occur in series with the most downstream external battery 4410, i.e. the external battery closest to the ventilator 4000, being recharged before the next external battery in the series. In such an arrangement each external battery is recharged along the series with the last or most upstream external battery 4420 being the last to be recharged.

FIG. 4*k* shows an arrangement where the AC PSU 4430 is not coupled to a device or ventilator 4000 but is used to recharge the external batteries 4410, 4420. In this arrangement the AC PSU 4430 is connected to a mains AC power supply 4434 to provide power to charge one or more external batteries, shown as charging two external batteries, an upstream external battery 4420 and a downstream external battery 4410. However, further external batteries may be connection in series between the upstream external battery 4420 and the downstream external battery 4410. In this configuration the downstream external battery 4410 is not connected to a device or ventilator 4000. In some arrangements according to the technology the external batteries are recharged in a series fashion along the series, for example the furthest downstream external battery 4410, i.e. the external battery that would be closest to the device 4000 when connected or furthest from the AC PSU 4430, may be recharged first and then the next external battery in the series may be recharged. The recharging scheme continues along the series until all the external batteries connected in the series are recharged, the last or most upstream external battery 4420 being the last to be recharged. It is to be understood that recharging may occur in a different order for example with the upstream external battery 4420 being recharged first and the downstream external battery 4410 being recharged last. In another arrangement all the external batteries may be recharged simultaneously.

If DC mains power 4460 is coupled to the ventilator 4000, irrespective of whether the internal battery is present or one or more external batteries are connected in series, see FIG. 4*m*, the DC mains power 4460 will have the power priority to provide the power supply to the device 4000. In such an arrangement the internal battery 4450, may also be charged by the DC mains power 4460 if sufficient power is available for recharging and running the device 4000. The power requirements for the running of the device 4000 take priority over the recharging of the internal battery 4450. In some arrangements the one or more external batteries 4410, 4420, if present, may not be recharged by the DC mains power 4460 irrespective of the level of DC power available. In other arrangements, if sufficient DC power is available, the external batteries 4410, 4420 may be recharged by the DC power. It is to be understood that the one or more external batteries 4410, 4420 are not required to be connected to the ventilator when the ventilator is connected to the DC mains power 4460. Preferably the internal battery 4450 is present within the ventilator 4000 when the ventilator is being powered by the DC mains power 4460 to provide a power backup as discussed above.

FIG. 4*l* illustrates an arrangement where one or more external batteries are used to run the ventilator or device 4000. The external batteries may be connected to the ventilator using an electrical cable, such as a DC power cord 4462, and each external battery is connected to the adjacent external battery using an electrical cable such as a DC power cord. Each external battery may include an input port and output port structured to receive the electrical cable between adjacent external batteries. The external battery closest to the device 4000 (e.g. a downstream external battery 4410), is connected to the power source connection of the device 4000 via an electrical cable, e.g. a DC power cord 4462. If more than one external battery is connected in series to the ventilator 4000 then an external battery power usage priority is used to determine from which external battery power will be supplied. The external battery being used to supply the power source to the ventilator in use may be considered the power supplying external battery.

In one arrangement the power from the external battery located furthest from the ventilator 4000 in the series, e.g. the upstream external battery 4420 as shown in FIG. 4*l*, will be used first to run the ventilator 4000, and will be the initial power supply external battery. Once the power has been substantially exhausted from the upstream external battery 4420 then the power will be used from the next external battery in the series and this external battery will become the power supplying external battery, e.g. the downstream external battery 4410 in FIG. 4*l*, to run the ventilator 4000. If more than two external batteries are connected in series to the ventilator 4000 then the power from each external battery will be used in series from the furthest or most upstream external battery along the series to the closest or most downstream external battery in the series. When all the power from all the external batteries has been substantially exhausted then the power in the internal battery 4450 will be used to run the ventilator 4000. In such an arrangement the power in the internal battery 4450 is the last to be used to allow a power safety backup should any power problems occur particularly when connected to AC mains power 4434 or DC mains power 4460.

In an alternative arrangement the external battery power usage priority may use the power from the external battery located closest to the ventilator 4000, i.e. the downstream external battery 4410, first and then use the power in the adjacent external battery in the series next and then continue along the series so that the external battery furthest from the ventilator 4000, i.e. the upstream battery 4420, is used last.

In a preferred aspect of the technology, the power usage and recharging are configured so that the internal battery 4450 is the last to be used and the first to be recharged.

6.6.2 Communication

In an aspect of the present technology the device or ventilator 4000 is configured to provide an estimate of the total remaining capacity or state of charge available from all coupled battery power sources, i.e. the internal battery 4450 and/or one or more external batteries 4410, 4420. The device 4000 may provide an estimate of a total capacity available as an estimate of the total run time remaining based on the present rate of power usage by the ventilator.

Each external battery has an input port and output port to relay communication signals or information along the chain to and from the controller of the ventilator 4000. Communication signals are relayed along the series from upstream external batteries 4410 to downstream external batteries 4410 back to the ventilator 4000 and in the reverse direction from the ventilator 4000 along the series to the most upstream external battery 4420. If the internal battery 4450 is present then the communication signals may also be provided through the internal battery 4450 or alternatively the internal battery 4450 may communicate independently with the ventilator controller.

The battery that is presently in use, i.e. being used to run the device, is configured to determine the remaining run time (hours) available for use as a function of the batteries present level of charge (milliAmperes (mA)) and the present rate of usage (mA/hr) being used by the ventilator. The other batteries, such as other external batteries and/or the internal battery, may each also determine their own remaining capacity and send this information to the battery that is currently powering the system. It is the battery that is currently powering the system that determines the current rate of power usage. It is to be understood that the time and rates may be provided in different units of time such as minutes or seconds instead of hours or as a combination of hours, minutes and/or seconds.

For example when the system is running from the most upstream external battery 4420 as shown in FIG. 4*l*, the controller 4230 of the ventilator 4000 may send a request for the remaining run time to the most upstream-battery 4420. The controller 4230 may send a request for battery capacity information to the internal battery 4450 as the most downstream battery coupled to the ventilator. The internal battery 4450 may then send a request to the downstream external battery 4410, i.e. the external battery connected closest to the ventilator 4000. The downstream external battery 4410 may then send a request for battery capacity information to the adjacent external battery and this continues along the series of external batteries to the most upstream external battery 4420 that is providing power or capable of providing power. The upstream external battery 4420 provides the remaining capacity (RC) information and the remaining run time (RRT) information based on the current rate of power usage by the ventilator from this upstream external battery 4420. The remaining capacity (RC) information and the remaining run time (RRT) information is passed back along the series to the downstream external battery 4410. The downstream external battery 4410 would also request the remaining capacity (RC) information from any other external batteries connected in the series between the upstream external battery 4410 and the downstream external battery 4410 if present, (not shown in FIG. 4*l*) to provide a total external batteries remaining capacity. In one arrangement the most downstream external battery 4410 may then send the information to the internal battery 4450, which also provides information regarding its own remaining capacity. The internal battery 4450 may determine an estimate of the total remaining run time (TRRT) or send the information to the controller 4230 to determine an estimate of the total remaining run time (TRRT). In this arrangement the internal battery 4450 or controller 4230 will estimate the total remaining run time (TRRT) using the following:

$$TRRT = \frac{(Bat(n)\_RC) + (Bat(n-1)\_RC) + \ldots + (Bat(1)\_RC)}{Bat(n)\_RC} \times BatnRRT \quad [1]$$

Wherein there are n number of batteries in the series and battery n is the most upstream battery (e.g the upstream external battery 4420 in FIGS. 4*j* to 4*m*) that is capable of providing power to run the ventilator 4000, such as when power is being provided by AC mains or DC mains, or is the battery being used to provide the power to run the ventilator 4000, TRRT is the total remaining run time for all of the n batteries in the series, Bat(n)_RC is the remaining capacity of the most upstream battery that has power available (e.g. the upstream external battery 4450 in FIG. 4*m*), Bat(n−1)_RC is the remaining capacity of the battery adjacent the most upstream battery (e.g. the downstream external battery 4410 in FIG. 4*m*), Bat(1)_RC is the remaining capacity of the most downstream battery (e.g. the internal battery 4450 in FIG. 4*m*) and BatnRRT is the Remaining Run Time of Battery n in hours (and/or minutes and/or seconds). It is to be understood that if there are batteries between the most downstream external battery n and the most upstream external battery then the calculation will also include the remaining capacity of each of the additional external batteries.

The remaining capacity in the above calculation [1] is preferably the actual battery remaining capacity in mA/hrs or some other absolute units rather than a percentage state of charge. This is due to the percentage state of charge may vary between batteries and over the life of the batteries such that errors may be introduced if percentage state of charge (SOC) is used. For example 100% SOC in one battery may be a different actual amount of mAhrs as the % SOC is relative to the maximum current available capacity in the pack which reduces with charge and discharge cycles, e.g. after 400 cycles the full capacity may only be 80% of the new pack capacity.

In an alternative arrangement the internal battery 4450 and the external batteries 4410, 4420 do not directly communicate with each other. The controller of the ventilator sends a signal to the downstream external battery 4410 to request the external battery remaining capacity and/or remaining run time for the series of external batteries. A determination of the total remaining run time of the external batteries is determined independently of a calculation of the total remaining run time of the internal battery 4450. In this arrangement the downstream external battery 4410 may perform the above calculation [1] to determine the total external battery remaining run time of all the external batteries based on the remaining capacity information received from all of the upstream external batteries in the series. Alternatively the upstream external battery 4420 may perform the calculation of total external battery remaining run time [1] based on received capacity information from all of the downstream external batteries in the series.

If the upstream external battery n has substantially discharged so that the power is being supplied from the next external battery downstream in the series, n−1, there will be no signal regarding charge from the upstream external battery n sent to the downstream external battery 4410. In this case the next external battery in the series n−1, becomes the n battery so only the charge remaining from the external battery presently providing the power or capable of providing power, n, and the other external batteries downstream from this external battery will be used in the calculation of the total remaining run time.

The controller of the ventilator may send an independent request signal to the internal battery 4450 for the internal battery remaining capacity and/or remaining run time. The internal battery 4450 may be configured to determine the remaining capacity of the internal battery 4450 and send this information to the controller.

In some arrangements the controller of the ventilator 4000 may be configured to receive the determined Total remaining run time information from all the battery sources, i.e. the internal battery and all the external batteries, as described above.

In other arrangements the controller may to be configured to receive the remaining capacity information from the internal battery 4450 and the series of external batteries 4410, 4420 and perform the calculation [1] above to determine the total battery remaining run time. The ventilator controller 4230 may be configured to display the total remaining run time estimate of all the battery sources on the user interface or display 4294 of the ventilator in hours and/or minutes and/or seconds. The ventilator 4000 may be configured to display the total remaining run time of each individual battery source or all external batteries and the internal battery in hours and/or minutes and/or seconds on the display 4292.

In a further aspect of the technology the controller of the ventilator may request an estimate of the total remaining capacity from coupled batteries, either from the external batteries and internal batteries together or from the external batteries and the internal battery independently. The ventilator may show the remaining capacity of the total battery sources, external batteries and/or internal batteries, in milliampere per hour (mA/hr) and/or as a percentage of remaining power based on the total level of power that the battery sources are capable of providing.

In one form of an aspect of the present technology the voltage supply is split to provide a first voltage rail and a second voltage rail from the main voltage rail, for example a 30V rail. The first voltage rail may be configured to supply power for the core ventilation system, i.e. to run the essential logic required to run the device 4000. The second voltage rail may be configured to supply power for the peripheral circuits. The peripheral circuits may include power to run the user interface such as the LCD or touch screen, data input/output devices such as USB or Ethernet or remote interfaces. In this arrangement failures or shut downs of the peripheral circuits are less likely to affect the core ventilation system, thus allowing the core ventilation to continue to run. In one example the first voltage rail and the second voltage rail may be 5V rails. Alternatively the first voltage rail and the second voltage rails may provide different voltage supply levels.

6.6.3 Power Efficiency

In a further aspect of the present technology the device or ventilator 4000 may include an energy regeneration system coupled to the main blower 4104. In this arrangement, see FIG. 4n, when the main blower is decelerated, such as when cycling from an inspiration set pressure to an expiration set pressure, the energy stored within the inertia of the blower may be stored in an energy storage unit 4510. The energy storage unit 4510 may include at least one capacitor, a group of capacitors or super capacitors or a battery. The energy storage unit 4510 is positioned in parallel with the input power supply 4210. The energy is regenerated or stored in the energy storage unit 4510 for use to run the device or components of the device 4000 for short periods of time in each breathing cycle until the energy in the energy storage unit has decayed to a set point. For example the short period of time may be approximately 200 to 500 milliseconds (ms), such as 300 ms. However, the duration depends on the energy recovered from the main blower inertia and the system operation current, i.e. the settings of the device at the time of energy regeneration. An optional diode 4520 as indicated by the dashed lines may be located between the energy storage unit 4510 and the input power supply 4210 depending upon whether the input power supply 4210 may tolerate excursions in the voltage from the energy storage unit 4510. In this arrangement the energy storage unit 4510 is only used to provide power to the main blower and the control system 4230 is powered from the power input supply.

In one aspect of the present technology when the energy storage unit 4510 is providing the power for running the ventilator 4000, a regulator switch switches off the power from the input power supply 4210. Switching off the input power supply when the device is being run from the energy storage unit increases the power efficiency of the system.

As shown in FIG. 4o, a voltage boost regulator 4530 is powered from the input power supply, which may include an external input supply 4540 and/or an internal battery 4450. Switches control whether the power is supplied from the external input supply 4540 or the internal battery 4450. The external input supply 4540 may include any one of the AC mains power 4434, DC Main power 4460 or an external battery 4420, 4410. The control of this switchover is performed by a battery charger internal circuit, when the external input supply drops below a first predetermined voltage such as approximately 10.5V, the system switches to the internal battery 4450, when the external input supply 4540 recovers and the voltage reaches above the first predetermined voltage or reaches a second predetermined voltage, such as approximately 11V, the system switches back to the external supply input 4540.

During motor deceleration, a motor driver 4105 continues to drive the main blower 4104 using a software control to maintain commutation of the motor but at a low drive level e.g. 10% drive. As the main blower 4104 decelerates then energy that is stored in the angular momentum and inertia of the main blower is transferred to a small amount of heat in the blower and motor control FETs and stored in the energy storage unit 4510, for example in 2×2700 uF motor capacitors. Consequently, the motor capacitor voltage increases from a first predetermined voltage limit, for example 30V, up to a maximum voltage, for example 45V. When the voltage boost regulator output exceeds a second predetermined voltage limit, for example 31V, the voltage boost regulator 4530 over voltage protection circuitry activates which turns off the voltage boost regulator 4530 which turns off the input power supply 4540, 4450. The system then runs from the energy stored on the energy storage unit 4510, for example the motor capacitors, until the voltage drops below the first predetermined voltage limit and the voltage boost regulator 4530 is restarted.

Advantageously, the energy recovered from the blower inertia is not instantly converted to heat so less heat dissipation is required. In addition, the energy recovered means the losses in the voltage boost regulator are turned off for the duration of time that the system is running from the energy storage unit. Hence reducing heat generation from the voltage boost regulator during high drive cases. Thus in aspects of the present technology the heat generated during deceleration of the main blower may be decreased due to the energy being stored in the energy storage unit 4510.

The increased power efficiency gained from recovering the main blower energy during deceleration and turning off the power input supply 4210 increases the efficiency of the internal battery 4450 and external batteries 4410, 4420, if present and being used as the present power source.

6.7 Alarm Systems

The device or ventilator 4000 may comprise an alarm system that provides visual and/or audible signals to provide an alert of some condition that requires attention. The ventilator 4000 may include output devices 4290 in the form of one or more audible alarms such as buzzers 4296 and/or one or more visual alarms, such as LEDs 4298 to provide an alert indication for an alarm condition. If multiple buzzers 4296 are present then each buzzer 4296 may produce a different alert sound or different volumes of sound and be used to indicate different types of alarm conditions. If multiple LED's 4298 are present each LED 4298 may have a different colour or level of brightness to indicate different types of alarm conditions.

The alarm conditions may include a range of different conditions that effect the device or therapy and may include a power supply issue (for example no internal battery attached, loss of external power supply, low battery, battery fault etc.), pressure supply issue (for example high pressure, high expiratory pressure, low PEEP, high PEEP, low peak inspiratory pressure, etc.), ventilation parameter issue (for example low or high tidal volume on inspiration or expiration, low or high minute ventilation on inspiration or expiration, low or high respiratory rate, occurrence of an apnea, etc.), Oximetry issues (for example low or high $SpO_2$ level, low or high pulse rate etc.), oxygen supply issues (only provided when an oxygen sensor is connected and may monitor low or high $FiO_2$), breathing circuit issues (for example high leak, incorrect circuit, pressure line disconnected, etc.) and system faults including faults with a blower, a sensor, battery communication, software, operating conditions etc.

The visual alarm may include the lighting or flashing of an alarm bar 4026 on the ventilator 4000 and or the sounding of an audible alarm in the ventilator 4000. An alarm message may be displayed on the user interface. There may be a priority of alarms, such as high, medium and low alarm and the alarm alert may vary for the different priority alarms. For example the high priority alarm may provide a red flashing light on the alarm bar 4026 and a first predetermined number of beeps of an audible alarm at a first predetermined frequency. A medium priority alarm may provide a yellow flashing light on the alarm bar 4026 and a second predetermined number of beeps of an audible alarm at a second predetermined frequency. A low priority alarm may provide a non-flashing light on the alarm bar 4026 and a third predetermined number of beeps of an audible alarm at a third predetermined frequency. The first predetermined number of beeps may be higher than the second predetermined number of beeps and the second predetermined number of beeps may be higher than the third predetermined number of beeps. Also the first predetermined frequency may be shorter than the second predetermined frequency and the second predetermined frequency may be shorter than the third predetermined frequency. However, it is to be understood other alarm priority arrangements may be used.

The volume of the audible alarms may be adjusted using the control settings available via the user interface on the device. The audible alarm may be temporarily muted for a predetermined time, such as 1, 2, 3, 4 or 5 minutes, by pressing a mute button on the user interface. If the alarm condition is still present after the muted predetermined time has passed then the audible alarm will sound again.

Some types of alarms, such as low priority and non-life threatening condition alarms may be manually reset by a user causing the visual and/or audible alarm to be turned off. Whilst other alarms may not be reset unless the alarm condition is corrected. Such critical alarms may be automatically reset by the ventilator upon correction of the alarm condition or reset enabled only after correction of the condition that caused the alarm.

In one aspect the system may be configured to attach a remote alarm 4660 to allow alarms to be placed at an alternative location to the ventilator 4000, for example in another room. The remote alarm 4660 is configured to alert carers of an alarm event. The remote alarm may be battery powered and connected to the device 4000 via a cable. Optionally a second remote alarm may be connected to the first remote alarm to enable placement of remote alarms in two separate locations.

In one aspect the system may be configured to attach a remote control 4650 that enables a user to operate an alarm as a nurse or carer alarm by pressing a button located on the remote control 4650. The remote control may be coupled to the device 4000 via a cable.

In one aspect of the present technology the alarm system includes a Hardware Alarm Controller (HAC) 4610. The HAC 4610 drives the alarm buzzers 4292 and/or LEDs 4294 to deliver the predetermined alarm patterns for the different alarm priorities as described above. FIG. 4p shows a schematic of the HAC control system. The HAC monitors the main board processor 4620 and the pneumatic block processor 4630. Although the main board processor and pneumatic block processor 4630 are shown as two different blocks in FIG. 4*p* it is to be understood that these may be present on a single PCB or on separate PCBs. The pneumatic block processor 4630 and the main board processor 4620 can communicate with each other to enable correct running of the device and therapies.

The Pneumatic block processor 4630 may also comprises a pneumatic block safety circuit 4632 that monitors the occurrence of hardware errors in the ventilator delivery system, such as pressure, current or temperature errors and software errors.

An alarm watchdog system monitors the main board processor 4620 and the pneumatic block processor 4630 and sends regular signals (2), (5), 4622, 4634 to the HAC to inform the HAC that the main board processor 4620 and the pneumatic block processor 4630 are functioning correctly. The pneumatic block safety circuit 4632 may generate the pneumatic block watchdog signal 4634. If the HAC 4610 does not receive either of the watchdog signals 4622, 4634 on time then the HAC raises an alarm and sends a safety assert state signal (6) to the pneumatic block processor 4630. The safety assert state signal (6) causes the system to be placed in a safe state. A safe state may include turning off the main blower 4104 and the PEEP Blower 4124, turning off the oxygen valve drive 4640 if present, deactivating the PEEP electrovalve 4136 and activating (energizing) the non-return valve 4114 and the safety valve 4085 (see FIG. 4O).

The HAC 4610 may also monitor the power supply for the ventilator 4000, via a signal 4670, for example a VCORE_Good signal, and will raise an alarm if power fails during operation of the ventilator 4000.

The HAC may be coupled to a HAC super capacitor (not shown) that is powered from a charger that runs from the first voltage rail as described above that is configured to run the core ventilation systems. Thus, the HAC and HAC super capacitor are considered part of the core ventilation system, i.e. are essential logic required to run the device 4000. The HAC super capacitor may be continually held fully charged while the system is being powered. The HAC super capacitor is configured to supply power to one or more of alarms 4290 if a power failure occurs to raise a total power failure alarm. Preferably the total power failure alarm is an audible alarm, and the HAC super capacitor is configured to power one or more of the buzzers 4292. Optionally the visual alarms may not be activated by the HAC super capacitor power to extend the run time on total power fail for the audible alarm.

The HAC 4610 has bi-directional communication with the main board processor 4620 as the main board processor 4620 software may be responsible for activating and deactivating the alarms based on predefined alarm algorithms that are designed for each type of alarm condition. The main board processor 4620 may then signal the HAC 4610 to activate the buzzers 4292 and/or LEDs 4294. Each alarm algorithm comprises inputs settings such as thresholds or parameter to be met to activate an alarm condition. Alarm activation parameters may be derived from the pneumatic block processor 4630 or the main board processor 4620. In certain arrangements the ventilator 4000 may include an Audio pause button 4610 that may allow some alarms to be muted by pressing the Audio pause button 4610 depending on the type and priority level of the alarm. When the Audio pause button 4610 is pressed a signal is sent to the HAC 4610 to turn off the output devices 4290, i.e. buzzers 4292 and/or LEDs 4294. A signal is also sent to the main board processor 4620 to advise of the paused alarm and start a timer for the paused alarm. The alarm will be restarted after a predetermined time has passed and the alarm condition has not been overcome. An audio pause LED may be present and be activated when an alarm is paused.

The remote alarm 4650 communicates with the main board processor 4620 to signal the activation of an alarm, i.e. a carer alarm. The main board processor 4620 may then signal the HAC 4610 to activate the buzzers 4292 and/or LEDs 4294 as required to raise the alarm alert.

The remote alarm 4610 is connected to the HAC 4610 so that any alarms raised by the HAC 4660 are sent to the remote alarm 4660.

6.8 Glossary

For the purposes of the present technology disclosure, in certain forms of the present technology, one or more of the following definitions may apply. In other forms of the present technology, alternative definitions may apply.

6.8.1 General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

6.8.2 Aspects of Devices

Air circuit: A conduit or tube constructed and arranged in use to deliver a supply of air or breathable gas between a device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation ($SaO_2$), partial pressure of carbon dioxide ($PCO_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Motor: A device for converting electrical energy into rotary movement of a member. In the present context the rotating member is an impeller, which rotates in place around a fixed axis so as to impart a pressure increase to air moving along the axis of rotation.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

Volute: The casing of the centrifugal pump that receives the air being pumped by the impeller, slowing down the velocity of flow of air and increasing the pressure. The cross-section of the volute increases in area towards the discharge port.

6.8.3 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate: The rate of spontaneous respiration of a patient, usually measured in breaths per minute.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

6.8.4 Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including $cmH_2O$, $g$-$f/cm^2$, hectopascal. $1 cmH_2O$ is equal to 1 $g$-$f/cm^2$ and is approximately 0.98 hectopascal. In this specification, unless otherwise stated, pressure is given in units of $cmH_2O$. For nasal CPAP treatment of OSA, a reference to treatment pressure is a reference to a pressure in the range of about 4-20 $cmH_2O$, or about 4-30 $cmH_2O$. The pressure in the patient interface is given the symbol Pm.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound power is usually given in decibels SPL, that is, decibels relative to a reference power, normally taken as $20 \times 10_{-6}$ pascal (Pa), considered the threshold of human hearing.

6.8.5 Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: A parameter of a ventilator that establishes the minimum respiration rate (typically in number of breaths per minute) that the ventilator will deliver to the patient, if not otherwise triggered.

Cycled: The termination of a ventilator's inspiratory phase and may also be known as Expiratory Trigger to indicate the start of expiration. When a ventilator delivers a breath to a spontaneously breathing patient, at the end of the inspiratory portion of the breathing cycle, the ventilator is said to be cycled to stop delivering the breath.

EPAP (or EEP): Expiratory Positive Airway Pressure (EPAP) is the pressure to be delivered to the patient during expiration or a base pressure, to which a pressure varying within the breath is added to produce the desired mask pressure which the ventilator will attempt to achieve during expiration.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation has a target ventilation, and which adjusts the level of pressure support to bring the patient ventilation towards the target ventilation.

Spontaneous/Timed (S/T)—A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the inspiratory portion of the breathing cycle by the patient's efforts.

Ventilator: A mechanical device that provides pressure support to a patient to perform some or all of the work of breathing.

6.8.6 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

6.8.7 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

6.9 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

7 ASPECTS

In the following, additional and/or alternative aspects of the invention are listed.

1. An apparatus for treating a respiratory disorder comprising:
   a housing;
   a user interface display;
   a pressure source to provide a supply of pressurized gas;
   a controller configured to control the pressure source;
   a power source connection configured to receive an electrical connection of a power source to provide a supply of power for the apparatus; and
   a plurality of external batteries electrically connected in a series to the power source connection.

2. The apparatus according to aspect 1, wherein the controller is configured to detect the connection of the plurality of external batteries and control the supply of power to the apparatus.

3. The apparatus according to any one of aspects 1 to 2, wherein in use the external battery of the plurality of external batteries being used to provide the supply of power for the apparatus is the power supplying external battery and each of the plurality of external batteries are used as the power source sequentially with the external battery closest to the power source connection being the last external battery to be used as the power source.

4. The apparatus according to any one of aspects 1 to 3, wherein each external battery of the plurality of external batteries is connected to an adjacent external battery using an electrical cable.

5. The apparatus according to any one of aspects 1 to 4, further comprising an internal battery configured to be received within the housing and in use the internal battery is used as the power source after all the power from the external batteries is depleted.

6. The apparatus according to any one of aspects 1 to 5, wherein an alternating current (AC) power supply is connectable in the series to the plurality of external batteries, and in use when the AC power supply is connected the AC power supply is used as the power source.

7. The apparatus according to any one of aspects 1 to 5, wherein a direct current (DC) power supply is connectable in the series to the plurality of external batteries, and in use when the DC power supply is connected the DC power supply is used as the power source.

8. The apparatus according to any one of aspects 1 to 7, wherein upon receiving a power capacity request from the controller each of the plurality of external batteries is capable of determining an estimate of its own remaining capacity.

9. The apparatus according to aspect 8, wherein the external batteries remaining capacity is used to determine an estimate of a total external batteries remaining run time.

10. The apparatus according to aspect 9, wherein the total external batteries remaining run time is determined as a function of the remaining capacity of each external battery and the remaining run time of the power supplying external battery.

11. The apparatus according to any one of aspects 8 to 10, wherein the plurality of external batteries includes an upstream external battery and a downstream external battery, wherein the downstream external battery is electrically connected to the power source connection and the upstream external battery is electrically connected in the series to the downstream external battery.

12. The apparatus according to aspect 11, wherein the downstream external battery is connected to the power source connection using an electrical cable.

13. The apparatus according to any one of aspects 10 or aspect 11, wherein one or more further external batteries are electrically connected between the downstream external battery and the upstream external battery.

14. The apparatus according to any one of aspects 11 to 13, wherein the upstream external battery is configured to send the determined estimate of the upstream external batteries remaining capacity to the downstream external battery.

15. The apparatus according to aspect 14, wherein each of the one or more further external batteries are configured to send the determined estimate of the external battery remaining capacity along the series to the downstream external battery.

16. The apparatus according to any one of aspects 14 to 15, wherein the downstream external battery is configured to determine a total external battery remaining capacity from all of the external batteries electrically connected in the series.

17. The apparatus according to any one of aspects 14 to 16, wherein the downstream external battery is configured to determine a total external battery remaining run time from all of the external batteries electrically connected in the series as a function of a remaining run time of the power supplying external battery.

18. The apparatus according to any one of aspects 5 and 6 to 17 when dependent upon aspect 5, wherein upon receiving a remaining capacity request from the controller the internal battery is capable of determining an estimate of the internal battery remaining capacity.

19. The apparatus according to aspect 18, wherein the internal battery remaining capacity is used to determine an estimate of internal battery remaining run time.

20. The apparatus according to aspect 19, wherein the internal battery remaining run time is determined as a function of a remaining run time of the internal battery when the internal battery is being used to provide the power to run the apparatus or the power supplying external battery when one of the plurality of external batteries is being used to run the apparatus.

21. The apparatus according to any one of aspects 18 to 20 when dependent upon any one of aspects 8 to 17, wherein the controller is configured to calculate an estimate of a total battery remaining capacity of the plurality of external batteries and the internal battery.

22. The apparatus according to any one of aspects 18 to 21 when dependent upon any one of aspects 8 to 17, wherein the controller is configured to calculate an estimate of a total battery remaining run time of the plurality of external batteries and the internal battery.

23. The apparatus according to any one of aspects 21 to 22, wherein the user interface display is configured to display the estimate of the total battery remaining capacity and/or the estimate of the total battery remaining run time.

24. The apparatus according to anyone of aspects 1 to 23, wherein the apparatus is a ventilator.

25. A method of determining an estimate of a total available battery capacity from two or more battery power sources electrically connected to a respiratory device, the respiratory device comprising a controller configured to perform the method of:
request an estimate of available capacity from a first battery power source to provide a first battery capacity;
request an estimate of available capacity from a second battery power source to provide a second battery capacity; and
combine the first battery capacity and the second battery capacity to determine an estimate of the total available battery capacity.

26. The method according to aspect 25, wherein the total available battery capacity is an estimate of a total state of charge from the first battery source and the second battery source.

27. The method according to any one of aspects 25 to 26, wherein the first battery source is at least one external battery electrically connected to the respiratory device and the second battery source is an internal battery located within the respiratory device.

28. The method according to aspect 27, wherein the first battery source includes a plurality of external batteries connected in series, each of the plurality of external batteries including an input port and output port configured to receive an electrical cable therebetween.

29. The method according to aspect 28, wherein the plurality of external batteries includes a downstream external battery, the output port of the downstream external battery is electrically coupled to the respiratory device via an electrical cable and the input port of the downstream external battery is electrically coupled via an electrical cable to the output port of a second external battery of the plurality of external batteries.

30. The method according to aspect 29, wherein each of the plurality of external batteries are electrically coupled to an adjacent external battery via an electrical cable connected between the input port of one of the plurality of external batteries and the output port of the adjacent external battery.

31. The method according to aspect 30 wherein each external battery provides an estimate of available capacity and sends the available capacity via the electrical cables along the series to the downstream external battery.

32. The method according to any one of aspects 25 to 31, wherein when the first battery source is the battery being used to provide power to the respiratory device, a total remaining run time is calculated as a function of the remaining run time of the first battery and the total available battery capacity.

33. The method according to any one of aspects 25 to 32, further comprising displaying the total available battery capacity on a user interface display of the respiratory device.

34. A respiratory device to provide a supply of breathable gas to a patient breathing in successive cycles, each cycle including an inspiration phase and an expiration phase, the respiratory device comprising:
a blower including a motor configured to accelerate to reach an inspiration pressure provided during the inspiration phase and decelerate to reach an expiration pressure provided during the expiration phase;
a first power source arranged to provide a supply of power to run the motor of the blower; and
an energy storage unit configured to store energy generated by the motor when the motor decelerates;
wherein when a voltage present in the energy storage unit exceeds a first threshold, the supply of power from the first power source to the motor is turned off and the motor is energized by the energy in the energy storage unit and when the voltage in the energy storage unit falls below a second threshold the supply of power from the first power source to the motor is turned on.

35. The respiratory device according to aspect 34, wherein the energy storage unit includes at least one capacitor or super capacitor.

36. The respiratory device according to aspects 34 to 35, further comprising a regulator switch that monitors the voltage of the energy storage unit and switches the supply of power to the motor from the first power source on and off.

The invention claimed is:

1. A respiratory device to provide a supply of breathable gas to a patient breathing in successive cycles, each cycle including an inspiration phase and an expiration phase, the respiratory device comprising:
a blower including a motor configured to accelerate to reach an inspiration pressure provided during the inspiration phase and decelerate to reach an expiration pressure provided during the expiration phase;
a first power source arranged to provide a supply of power to run the motor of the blower; and
an energy storage unit configured to store energy generated by the motor when the motor decelerates;
wherein when a voltage present in the energy storage unit exceeds a first threshold, the supply of power from the first power source to the motor is turned off and the motor is energized by the energy in the energy storage unit and when the voltage in the energy storage unit falls below a second threshold the supply of power from the first power source to the motor is turned on.

2. The respiratory device according to claim 1, wherein the energy storage unit includes at least one capacitor or super capacitor.

3. The respiratory device according to claim 1, further comprising a regulator switch that monitors the voltage of the energy storage unit and switches the supply of power to the motor from the first power source on and off.

4. The respiratory device according to claim 2, further comprising a regulator switch that monitors the voltage of the energy storage unit and switches the supply of power to the motor from the first power source on and off.

5. The respiratory device according to claim 3, wherein the regulator switch is a voltage boost regulator.

6. The respiratory device according to claim 1, wherein the energy storage unit includes at least one capacitor, a group of capacitors or super capacitors, or a battery.

7. The respiratory device according to claim 1, further comprising a control system.

8. The respiratory device according to claim 1, wherein the energy storage unit is positioned in parallel with the first power source.

9. The respiratory device according to claim 1, wherein a diode is located between the energy storage unit and the first power source.

10. The respiratory device according to claim 1, wherein the first power source includes an external input supply and/or an internal battery.

11. The respiratory device according to claim 10, wherein the external input supply includes any one of an AC mains power supply, DC Main power supply, or an external battery.

12. The respiratory device according to claim 1, further comprising a motor driver.

13. A method of operating a respiratory device to provide a supply of breathable gas to a patient breathing in successive cycles, each cycle including an inspiration phase and an expiration phase, the method comprising:
providing a blower including a motor configured to accelerate to reach an inspiration pressure provided during the inspiration phase and decelerate to reach an expiration pressure provided during the expiration phase;
providing a first power source arranged to provide a supply of power to run the motor of the blower;
storing energy generated by the motor in an energy storage unit when the motor decelerates;
turning off the supply of power from the first power source to the motor when a voltage present in the energy storage unit exceeds a first threshold and energizing the motor by the energy stored in the energy storage unit; and
turning on the supply of power from the first power source to the motor when the voltage in the energy storage unit falls below a second threshold.

14. The method according to claim 13, wherein energy generated by the motor is stored in the energy storage unit when the motor cycles from an inspiration pressure to an expiration pressure.

15. The method according to claim 13, wherein a diode is located between the energy storage unit and the first power source, and the diode is used to provide power to the blower.

16. The method according to claim 13, further comprising a control system that is powered from the first power source.

* * * * *